(12) United States Patent
Chanot et al.

(10) Patent No.: US 9,975,838 B2
(45) Date of Patent: May 22, 2018

(54) METHOD FOR SYNTHEZISING CYCLOHEXENONES FOR USE IN THE PERFUME INDUSTRY AND COMPOUNDS OBTAINED THEREBY

(71) Applicant: V. MANE FILS, Le Bar sur Loup (FR)

(72) Inventors: Jean-Jacques Chanot, Speracedes (FR); Caroline Plessis, Chateauneuf (FR)

(73) Assignee: V. MANE FILS, Le Bar sur Loup (FR)

( * ) Notice: Subject to any disclaimer, the term of this patent is extended or adjusted under 35 U.S.C. 154(b) by 0 days. days.

(21) Appl. No.: 15/453,597

(22) Filed: Mar. 8, 2017

(65) Prior Publication Data

US 2017/0174602 A1 Jun. 22, 2017

Related U.S. Application Data

(62) Division of application No. 14/432,549, filed as application No. PCT/FR2013/052235 on Sep. 24, 2013, now Pat. No. 9,701,607.

(30) Foreign Application Priority Data

Oct. 5, 2012 (FR) ...................... 12 59524

(51) Int. Cl.
  *A61K 8/18* (2006.01)
  *A61K 8/00* (2006.01)
  *C07C 49/603* (2006.01)
  *C07C 35/18* (2006.01)
  *C07C 69/145* (2006.01)
  *C07C 43/188* (2006.01)
  *C11B 9/00* (2006.01)

(52) U.S. Cl.
  CPC ............ *C07C 49/603* (2013.01); *C07C 35/18* (2013.01); *C07C 43/188* (2013.01); *C07C 69/145* (2013.01); *C11B 9/0034* (2013.01); *C07C 2101/08* (2013.01); *C07C 2101/10* (2013.01); *C07C 2101/14* (2013.01); *C07C 2101/16* (2013.01)

(58) Field of Classification Search
  None
  See application file for complete search history.

(56) References Cited

FOREIGN PATENT DOCUMENTS

JP 2008-127333 * 6/2008

OTHER PUBLICATIONS

Yano et al, JP 2008-127333, Jun. 5, 2008.*

* cited by examiner

*Primary Examiner* — Jessica Whiteley
(74) *Attorney, Agent, or Firm* — B. Aaron Schulman, Esq.; Stites & Harbison, PLLC

(57) ABSTRACT

Cyclohexenone and cyclohexenol compounds are provided having specific fragrances and remanence properties, along with methods for synthesizing these compounds, including obtaining the compound by condensing a ketone on an α-methylene-aldehyde in order to obtain, by means of a domino reaction, compounds of formula (II) as follows:

(II)

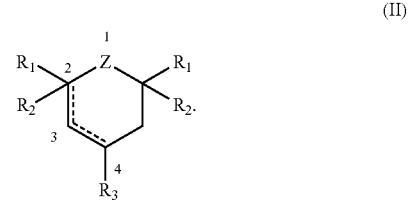

14 Claims, No Drawings

METHOD FOR SYNTHEZISING CYCLOHEXENONES FOR USE IN THE PERFUME INDUSTRY AND COMPOUNDS OBTAINED THEREBY

CROSS REFERENCE TO RELATED APPLICATIONS

This application is a divisional of U.S. Ser. No. 14/432,549, having a filing date of Aug. 26, 2015, which was a 371 application of International application PCT/FR2013/052235, filed Sep. 24, 2013, which claimed the benefit of French Patent application 1259524, filed Oct. 5, 2012, all of said applications incorporated herein by reference.

FIELD OF THE INVENTION

The present invention relates to a simple, inexpensive and reliable, novel method of synthesis of cyclohexenone and cyclohexenol compounds, said compounds being able to be used in the perfumery, cosmetics and detergent industries particularly, said compounds having particular fragrances and properties of persistence of scent.

BACKGROUND OF THE INVENTION

Cyclohexenones and cyclohexenols are important families of compounds in the perfume and aromas industry. Many compounds belonging to these families have been described and synthesised, like for example Celery Ketone, or the compounds described in patents EP 0504592 (Firmenich) or JP 2008127333 (Kao Corp). However, for these latter, one of the technical problems relating to this type of compound resides in their method of synthesis. For example, patent EP 0504592 describes a method of synthesis of cyclohexenones by condensation between an alkyl vinyl ketone and a carbonyl derivative. This method has disadvantages, particularly in that it is difficult to implement, that the reactions which take place are unstable and that it has a high cost (due to the high cost of the starting materials). However the main problem of this method resides in its dangerous nature when it is put into practice due to the alkyl vinyl ketone. Another method which has been implemented in the prior art consists in causing a β-ketoester to react with a methylene aldehyde. This type of method is particularly described in the patent application JP 2008127333. However, here again, the starting substrates have a high cost (particularly the β-ketoester which has to be synthesised with different substituents) and above all the method is difficult to industrialise. Now, the perfumes and aromas industry has a constant need to find novel molecules in order to best deal with an increasing number of constraints (environmental constraints, regulatory constraints, economic constraints, etc.).

SUMMARY OF THE INVENTION

To this end, in order to be able to easily obtain novel fragrant and/or aromatic compounds, the Applicant has developed a novel method of synthesis of cyclohexenone and cyclohexenol compounds. Not only is the method in question novel and inventive, but it also makes it possible to obtain a large number of compounds, which are themselves novel and inventive, in addition to compounds already known in the prior art. The method according to the present invention consists in the condensation of a ketone on an α-methylene aldehyde in order to obtain by a domino reaction, cyclohexenone compounds of formula (I) below:

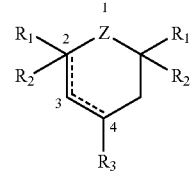

(I)

in which:
R1 represents a methyl or an ethyl;
R2 represents independently a hydrogen or a C1-C5 alkyl or C2-C5 alkenyl group;
R3 represents an alkyl or alkenyl group, optionally substituted by an aryl, or R3 represents a cyclic alkyl or cyclic alkenyl group, optionally substituted by one or more C1-C6 alkyl groups, it being understood that R3 includes in total 3 to 10 carbon atoms;
Z represents C(O) or CR4(OR5), with
R4 represents a hydrogen or a C1-C8 alkyl or C2-C8 alkenyl group;
R5 represents a hydrogen or a C1-C8 alkyl or alkanoyl or C2-C8 alkenyl or alkenoyl group;
knowing that a double bond is present or absent in the ring and that when it is present, it is
either in position 2-3 and R2 is absent in position 2,
or in position 3-4 and R2 is present in position 2 and is such as defined above.

To the knowledge of the Applicant, this type of reaction has never been described before. On completion of this first reaction step, it is possible to obtain different types of cyclohexenone derivatives, as well as cyclohexenol compounds. The method according to the present invention is novel and inventive relative, particularly, to that described in U.S. Pat. No. 4,326,997 in which compounds presenting close structures are described. In addition, the method described in said patent does not allow all the compounds of formula (I) to be obtained while the present method allows it. Lastly, the method according to the present invention has the advantage of being simple, inexpensive (through the use of cheap substrates), without risks, and of being easily industrialisable and of presenting a good yield.

The present invention also has as its object compounds as well as their use in perfumery, characterised in that said compounds respond to the following general formula (II):

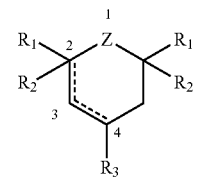

in which:
R1 represents a methyl or an ethyl;
R2 represents independently a hydrogen or a C1-C5 alkyl or C2-C5 alkenyl group;
R3 represents an alkyl or alkenyl group, optionally substituted by an aryl, or R3 represents a cyclic alkyl or cyclic alkenyl group, optionally substituted by one or more C1-C6 alkyl groups, it being understood that R3 includes in total 7 to 10 carbon atoms;

Z represents C(O) or CR4(OR5), with
R4 represents a hydrogen or a C1-C8 alkyl or C2-C8 alkenyl group;
R5 represents a hydrogen or a C1-C8 alkyl or alkanoyl or C2-C8 alkenyl or alkenoyl group;

knowing that a double bond is present or absent in the ring and that when it is present, it is
either in position 2-3 and R2 is absent in position 2,
or in position 3-4 and R2 is present in position 2 and is such as defined above; said compound being in the form of a stereoisomer or of a mixture of stereoisomers, or of a racemic mixture.

U.S. Pat. No. 4,326,997 describes fragrant compounds close to the general formula (II), particularly cyclohexenone and cyclohexenol compounds including an R3=(CH2)2-i-Pr group and the following olfactive descriptions: balsamic, woody, sweet, earthy, herbaceous . . . which descriptions are different from those of the compounds presently claimed.

A scientific publication by L. A. Khejfik et al. (*Parf. Cosm. Sav.* vol. 8, No. 8, August 1965) describes cyclohexenone and cyclohexenol compounds including R3 groups having 6 carbon atoms. However, these compounds are described as having iris-ionone notes and not sandalwood, woody or green notes as is the case for the derivatives of the invention.

A third object of the present invention relates to compositions comprising compounds of formula (II).

A last object of the present invention relates to the use of compounds of the following formula (III):

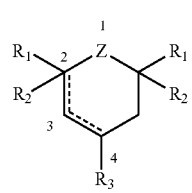

(III)

in which:
R1 represents a methyl or an ethyl;
R2 represents independently a hydrogen or a C1-C5 alkyl or C2-C5 alkenyl group;
R3 represents an alkyl or alkenyl group, optionally substituted by an aryl, or R3 represents a cyclic alkyl or cyclic alkenyl group, optionally substituted by one or more C1-C6 alkyl groups, it being understood that R3 includes a total of 3 to 10 carbon atoms and that it includes at least one unsaturation when it contains 5 to 6 carbon atoms;

Z represents C(O) or CR4(OR5), with
R4 represents a hydrogen or a C1-C8 alkyl or C2-C8 alkenyl group;
R5 represents a hydrogen or a C1-C8 alkyl or alkanoyl or C2-C8 alkenyl or alkenoyl group;

knowing that a double bond is present or absent in the ring and that when it is present, it is
either in position 2-3 and R2 is absent in position 2,
or in position 3-4 and R2 is present in position 2 and is such as defined above.

The term "alkyl" within the meaning of the present invention designates a linear or branched saturated hydrocarbon group, preferably having from 1 to 10 carbon atoms.

As examples of alkyl groups it is possible to cite particularly methyl, ethyl, n-propyl, i-propyl, n-butyl, i-butyl, t-butyl, pentyl and hexyl groups.

The expression "cyclic alkyl" designates a cyclic saturated hydrocarbon group, preferably having from 3 to 10 carbon atoms. Preferably, the group comprises 5 to 6 carbon atoms, and still more preferably 5 carbon atoms. As examples of cyclic alkyl groups, it is particularly possible to cite cyclopentyl.

The term "alkenyl", within the meaning of the present invention, designates a linear or branched unsaturated hydrocarbon group containing at least one carbon-carbon double bond and preferably having from 2 to 10 carbon atoms. As examples of alkenyl groups, it is particularly possible to cite vinyl, allyl, methallyl, 2-propenyl, isopropenyl, 2-butenyl, 3-butenyl, 2-pentenyl, 3-pentenyl, 4-pentenyl, 1-hexenyl, etc. groups.

The expression "cyclic alkenyl" designates a cyclic unsaturated hydrocarbon group, preferably having from 3 to 10 carbon atoms. As examples of cyclic alkenyl groups it is particularly possible to cite cyclopentenyl.

The term "alkanoyl", within the meaning of the present invention, designates a —C(O)— alkyl group, derived from a carboxylic acid, in which the alkyl group is such as defined above. As examples of alkanoyl groups it is particularly possible to cite formyl, acetyl, propionyl, butyryl, etc. groups.

The term "alkenoyl", within the meaning of the present invention, designates a —C(O)— alkenyl group, derived from a carboxylic acid, in which the alkenyl group is such as defined above. As examples of alkenoyl groups it is particularly possible to cite particularly 2-propenoyl, 2-butenoyl, 2-methyl-2-propenoyl, etc.

The term "aryl" designates a functional hydrocarbon group derived from an aromatic hydrocarbon having from 6 to 14 carbon atoms, preferably from 6 to 10 carbon atoms. As examples of aryl group it is possible to cite particularly the phenyl, tolyl, naphthyl, xylyl groups.

DETAILED DESCRIPTION OF EXEMPLARY EMBODIMENTS

A first object of the present invention therefore relates to a method of preparation of a compound of formula (I) such as described above comprising the following steps:

i) reaction of an α-methylene aldehyde, in the presence of a base, with a symmetrical ketone to obtain a compound of formula (Ia) in which R1 and R3 are such as defined above, R2 is a hydrogen and a double bond is present at 2-3 or 3-4 in the ring and this reaction being optionally followed by steps ii), and/or iii), and/or iv), ii) mono- or bis-alkylation reaction in order to obtain a compound of formula (Ia) in which R2 is a C1-C5 alkyl or C2-C5 alkenyl group;

iii) conversion of the Z=C(O) function of the compound obtained in the preceding step into a Z=CR4(OR5) function, R4 and R5 being such as defined above;

iv) reduction of the double bond at 2-3 or 3-4 present in the ring of the compound obtained in the preceding step, step iv) being able to be performed after any one of steps i), ii), or iii).

The diagram below represents step i) of the method such as described above.

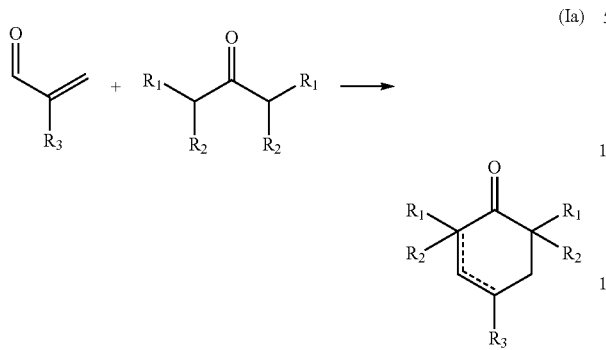

To the knowledge of the Applicant, this type of reaction has never been reported.

Only domino reactions of Robinson annulation type between a carbonyl derivative and methyl vinyl ketone (EP 0504592 Firmenich) or reactions by means of a β-ketoester (JP 2008127333) have been described.

Step i) between α-methylene aldehyde and a symmetrical ketone is performed in the presence of a base. The base which can be used can be selected from inorganic bases (KOH, NaOH, LiOH . . . ) or organometallic bases (t-Bu-OK, MeONa . . . ). The solvents which can be used in the present reaction are particularly water, ethanol, methanol, toluene, cyclohexane or THF . . . in mixture or otherwise. Preferably, a water/ethanol mixture will be used. This reaction step i) can be performed at ambient temperature with reflux of the solvent, preferably between 50 and 70° C.

Following the formation of the compound of formula (Ia) on completion of step i), an optional additional step ii) allows compounds to be obtained of formula (Ia) such as described above, in which R2 is a C1-C5 alkyl or C2-C5 alkenyl group. A first mono-alkylation step ii) allows a compound to be obtained of formula (Ia) having an alkylated or alkenylated group R2 in position 6 of the ring, the 2-3 double bond being present. The same compounds can be alkylated a second time in order to give compounds of formula (Ia) in which R2 is an alkyl or an alkenyl in positions 2 and 6 of the ring; in this case the double bond of the ring is in position 3-4 (the groups R1 and R3 being defined as above).

Step ii) is optionally followed by a step iii) of conversion of a compound of formula (Ia) obtained on completion of steps i), ii) or iv) into a compound of formula (I) in which R1, R2 and R3 are such as defined above, and Z=CR4 (OR5). The method according to the invention optionally comprises a step iv) of reduction of the double bond present in the ring at 2-3 or 3-4 of the compound obtained in the preceding step, step iv) being able to be performed after any one of steps i), ii) or iii). The following paragraphs detail the different steps allowing the compounds of formula (I) to be obtained.

In a first embodiment of the invention, step iii) comprises a step iii.a) of reduction of the ketone function of the compound of formula (Ia) obtained in steps i), ii) or iv) in order to obtain a compound of formula (Ib) such as represented in the diagram below, with R1, R2, R3 such as defined above in step i) and/or iv) and Z=CR4(OR5) with R4 represents an H or a C1-C8 alkyl or C2-C8 alkenyl, R5 represents an H and the double bond at 2-3 or 3-4 being absent in the case in which step iv) is performed before step iii.a).

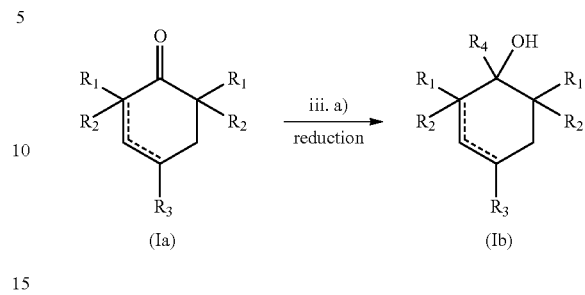

Preferably, step iii.a) of reduction is performed by addition of an organomagnesium R4MgX or of a metallic hydride (R4=H).

In addition to step iii.a), the method can comprise a step iii.b) of alkylation of the alcohol function of the compound (Ib) obtained in step iii.a), in order to obtain a compound of formula (Ic) with R1, R2, R3 such as defined above in step i) and/or iv) and Z=CR4(OR5) with R4 represents an H or a C1-C8 alkyl or C2-C8 alkenyl, R5 represents an alkyl or an alkenyl (classical Williamson reaction) and the double bond at 2-3 or 3-4 being absent in the case in which step iv) is performed before step iii.b). This step iii.b) is represented in the diagram below.

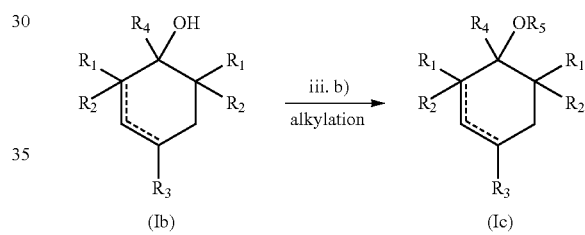

This alkylation step permits compounds of formula (I) to be obtained comprising Z=CR4(OR5) with R4 representing an H or a C1-C8 alkyl or C2-C8 alkenyl and R5 representing an alkyl or an alkenyl.

Preferably, the alkylation step iii.b) is performed by addition of an alkyl halide such as MeI, EtI, allyl bromide etc.

In another embodiment of the invention, step iii) comprises, in addition to step iii.a) such as defined above, a step iii.c) of esterification of the alcohol function of the compound (Ib) obtained in step iii.a), in order to obtain a compound (Id) having R1, R2, R3 such as defined above in step i) and/or iv) and Z=CR4(OR5) with R4 represents an H or a C1-C8 alkyl or C2-C8 alkenyl, and R5 represents an alkanoyl or an alkenoyl, the double bond at 2-3 or 3-4 being absent in the case in which step iv) is performed before step iii.c) (see diagram below).

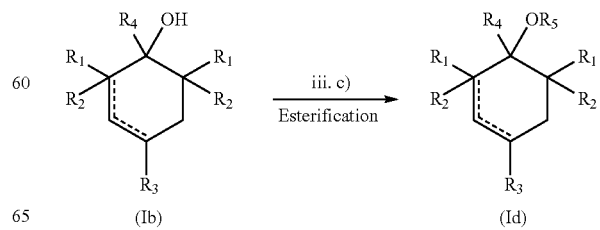

Preferably, esterification step iii.c) is performed by addition of an anhydride or of an acyl chloride R'C(O)Cl with R' representing a hydrogen, or a C1-C7 alkyl, or a C2-C7 alkenyl.

The method according to the invention can comprise a step iv) of reduction of the double bond at 2-3 or at 3-4 in the ring. This step can be performed after step i), ii) or iii). It is preferably performed after step i).

In a particular embodiment of the invention, the compounds of formula (Ia) with Z=C(O) and comprising a double bond at 2-3 can be transformed, by a step iv) of selective reduction, into compounds (Ie) in which the double bond in the ring is absent, the function Z=C(O) being retained (see diagram below). This step of reduction iv) can be performed for example in the presence of complexes using copper or rhodium, or according to any other method well known to the man of the art.

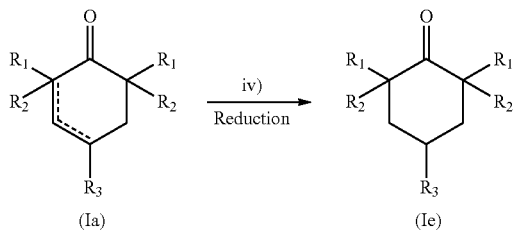

(Ia)  (Ie)

In another particular embodiment of the invention, the compounds of formula (Ia) having Z=C(O) and comprising a double bond at 2-3 or at 3-4 can be transformed, by a step iv) of reduction, into compounds in which the double bond in the ring is absent and that of the function Z=C(O) is retained. Preferably, this step iv) of reduction is performed in the presence of hydrogen and of a Pd/C catalyst. In this case, the compounds obtained carry no double bond, and all the alkenyl or cyclic alkenyl groups R1, R2, R3 optionally present are hydrogenated into corresponding alkyl groups.

The step of reduction can also be performed under hydrogen pressure in the presence of Raney nickel in order to give compounds of formula (I) in which the double bond in the ring is absent, all the alkenyl or cyclic alkenyl groups R1, R2, R3 optionally present are hydrogenated into corresponding alkyl groups, and Z=CH(OH).

Thus, the method according to the invention such as described above allows all the compounds responding to the general formula (I) to be obtained.

A second object of the present invention relates to a compound of the following general formula (II):

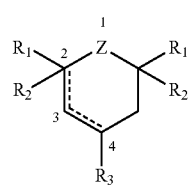

(II)

in which:
R1 represents a methyl or an ethyl;
R2 represents independently a hydrogen or a C1-C5 alkyl or C2-C5 alkenyl branched or linear group;
R3 represents an alkyl or alkenyl group optionally substituted by an aryl, or R3 represents a cyclic alkyl or cyclic alkenyl group optionally substituted by one or more C1-C6 alkyl groups, it being understood that R3 includes in total 7 to 10 carbon atoms;
Z represents C(O) or CR4(OR5), with
R4 represents a hydrogen or a C1-C8 alkyl or C2-C8 alkenyl group;
R5 represents a hydrogen or a C1-C8 alkyl or alkanoyl or C2-C8 alkenyl or alkenoyl group,
knowing that a double bond is present or absent in the ring and that when it is present, it is
either in position 2-3 and R2 is absent in position 2,
or in position 3-4 and R2 is present in position 2 and is such as defined above; said compound being in the form of a stereoisomer or of a mixture of stereoisomers, or of a racemic mixture.

All the compounds of general formula (II) can be obtained by means of the method described above.

In a particular embodiment of the invention, R3 is either a cyclopentyl group substituted by one or more alkyl groups, or a cyclopentenyl group substituted by one or more alkyl groups, particularly a methyl.

In a second embodiment of the invention, R3 is an alkyl or alkenyl group, optionally substituted by an aryl. Preferably, R3 is substituted by a phenyl.

Preferably, the compounds of formula (II) are cyclohexenones and therefore have a Z=C(O).

Still more preferably, the compounds of formula (II) have a Z=CR4(OR5) with R4 represents a hydrogen or a C1-C8 alkyl or C2-C8 alkenyl group, and R5 represents a hydrogen.

A third object of the present invention relates to a composition comprising at least one compound of general formula (II) such as defined above in the form of a stereoisomer or of a mixture of stereoisomers, or of a racemic mixture.

According to a particular embodiment, the composition is characterised in that it comprises in addition at least one other fragrancing substance.

The effective quantity of the compounds of formula (II) according to the invention incorporated in the composition will vary depending on the nature of the composition, the required fragrancing effect, and the nature of the other compounds, fragrancing or not, optionally present, and will be able to be determined easily by the man skilled in the art, knowing that it can vary within a very broad range, from 0.1 to 99% by weight, in particular from 0.1 to 50% by weight, particularly from 0.1 to 30% by weight relative to the total weight of the composition.

The invention also relates in particular to a cosmetic composition, particularly a face and body cream, talcum powder, hair or body oil, shampoo, hair lotion, bath salt, bath oil, shower gel, bath gel, toilet soap, body antiperspirant, body deodorant, lotions, shaving cream, shaving soap, cream, toothpaste, mouthwash, ointment comprising at least one compound of formula (II), or at least one composition comprising at least one compound of formula (II).

The invention also relates to a cleaning product, particularly softener, detergent, washing powder, air freshener, comprising at least one compound of formula (II) or at least one composition comprising at least one compound of formula (II).

The compound or compounds according to the invention can be used, alone or in combination, as such or be incorporated in or on an inert support material or a material which can contain other active ingredients of the finished composition. A large variety of support materials can be used including, for example, polar solvents, oils, greases, finely divided solids, cyclodextrins, maltodextrins, gums, resins and any other known support material for such compositions.

A last object of the present invention relates to the use as fragrancing agent of a compound of the following formula (III):

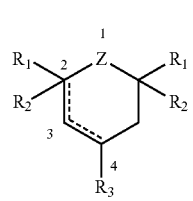

in which:
R1 represents a methyl or an ethyl;
R2 represents independently a hydrogen or a C1-C5 alkyl or C2-C5 alkenyl group;
R3 represents alkyl or alkenyl, optionally substituted by an aryl, or R3 represents a cyclic alkyl or cyclic alkenyl group optionally substituted by one or more C1-C6 groups, it being understood that R3 includes in total 3 to 10 carbon atoms and that it includes at least one unsaturation when it contains 5 to 6 carbon atoms;
Z represents C(O) or CR4(OR5), with
R4 represents a hydrogen or a C1-C8 alkyl or C2-C8 alkenyl group;
R5 represents a hydrogen or a C1-C8 alkyl or alkanoyl, or C2-C8 alkenyl or alkenoyl group;
knowing that a double bond is present or absent in the ring and that when it is present, it is
either in position 2-3 and R2 is absent in position 2,
or in position 3-4 and R2 is present in position 2 and is such as defined above.

The compounds of formula (III) can be used as an odour-masking agent or as an odour-neutralising agent. The term "fragrant" is used here to designate any organoleptic compound stimulating the sense of smell in a pleasant manner. The term "masking agent" or "masking" is understood to mean reducing or eliminating the perception of a bad odour generated by one or more molecules entering into the composition of a product. "Odour-neutralising agent" is understood to mean neutralising, destroying or absorbing a bad odour fixed in the atmosphere or on a support (such as a fabric). Indeed, to almost any odour there corresponds another odour, which, mixed with the first in a certain proportion, cancels it out.

In addition, said compound can be used alone or in combination with at least one other aromatising or perfuming ingredient, and/or at least one solvent, and/or at least one adjuvant. The additional fragrancing agent or agents can be compounds of formula (I) or other fragrancing agents known to the man skilled in the art who will be able to make a selection depending on the sought-after effect.

Generally, the compounds according to the invention will be used in the field of perfumery. "Perfumery" is understood to mean not only perfumery in the usual meaning of the term, but also the other fields in which the odour of the products is important. It may concern perfumery compositions in the usual meaning of the term, such as perfuming bases and concentrates, eaux de Cologne, eaux de toilette, perfumes and similar products; topical compositions—in particular cosmetics—such as face and body creams, talcum powders, hair oils, shampoos, hair lotions, bath salts and oils, shower and bath gels, toilet soaps, body anti-perspirants and deodorants, shaving lotions and creams, soaps, creams, toothpastes, mouthwashes, ointments, and similar products; and cleaning products, such as softeners, detergents, washing powders, air fresheners, and similar products.

A particular embodiment of the invention resides in the use of a compound of formula (III) to modify or strengthen the organoleptic properties of a substance, of a composition or of an article.

"Organoleptic properties" is understood to mean any property able to modify, improve or strengthen the organoleptic perception of a substance, of a composition, of an article by a user. Thus, by way of preferred example, the organoleptic agent according to the invention can consist in a perfuming agent able to confer, modify, improve or strengthen the olfactive perception of a substance, of a composition or of an article.

The general principle of the invention is based on the preparation of the compounds of formula (I), the novel compounds of formula (II), as well as the use in perfumery of the compounds of formula (III) described above. The following examples illustrate a particular manner of preparing the compounds of the invention, as well as the olfactive profile of each of the compounds given by way of example. These examples are only given for illustration and must not be understood as limiting the general scope of the invention. The following table gives all of the chemical structures of the compounds synthesised according to the invention.

TABLE 1

| Structure of the synthesised compounds | |
| --- | --- |
| Example No. | Chemical structure |
| Example 1 | |
| Example 2 | |
| Example 3 | |
| Example 4 | |

TABLE 1-continued

Structure of the synthesised compounds

| Example No. | Chemical structure |
|---|---|
| Example 5 | 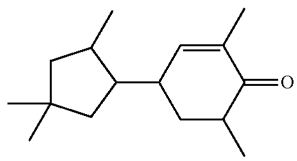 [SMILES: CC1=CC(C2CC(C)(C)CC2C)CC(C)C1=O] |
| Example 6 | 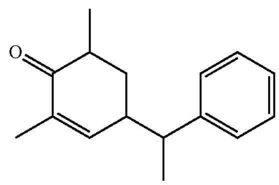 [SMILES: CC1=CC(C(C)c2ccccc2)CC(C)C1=O] |
| Example 7 | 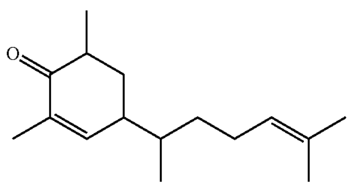 [SMILES: CC(C)=CCCC(C)C1C=C(C)C(=O)C(C)C1] |
| Example 8 | 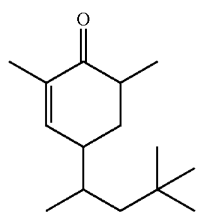 [SMILES: CC1=CC(C(C)CC(C)(C)C)CC(C)C1=O] |
| Example 9 | 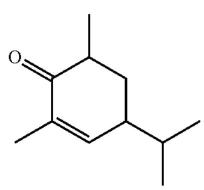 |
| Example 10 | 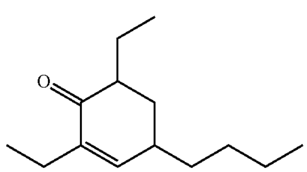 |
| Example 11 | 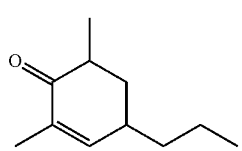 |
| Example 12 | 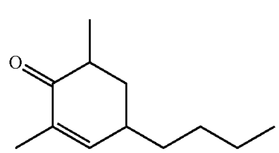 |
| Example 13 | |
| Example 14 | |
| Example 15 | (S) |
| Example 16 | |
| Example 17 | |
| Example 18 | |
| Example 19 | (R) |
| Example 20 | |

TABLE 1-continued

Structure of the synthesised compounds

| Example No. | Chemical structure |
|---|---|
| Example 21 | 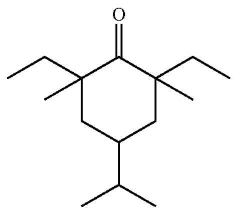 [SMILES: CCC1(C)CC(C(C)C)CC(C)(CC)C1=O] |
| Example 22 | 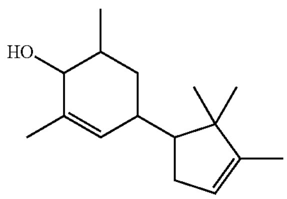 [SMILES: CC1=CC(C2CC=C(C)C2(C)C)CC(C)C1O] |
| Example 23 | 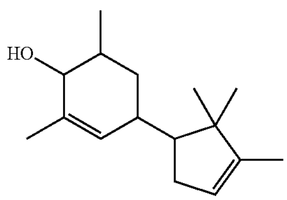 [SMILES: CC1=CC(C2CC=C(C)C2(C)C)CC(C)C1O] |
| Example 24 | 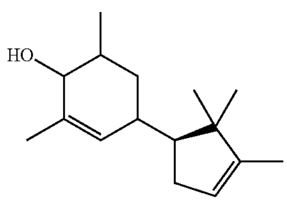 [SMILES: CC1=CC([C@@H]2CC=C(C)C2(C)C)CC(C)C1O] |
| Example 25 | 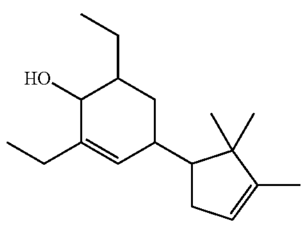 [SMILES: CCC1=CC(C2CC=C(C)C2(C)C)CC(CC)C1O] |
| Example 26 | 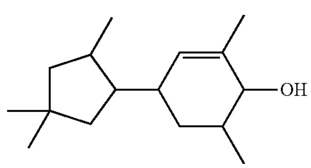 [SMILES: CC1=CC(C2CC(C)(C)CC2C)CC(C)C1O] |
| Example 27 | 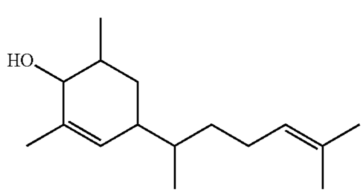 [SMILES: CC(C)=CCCC(C)C1C=C(C)C(O)C(C)C1] |
| Example 28 | 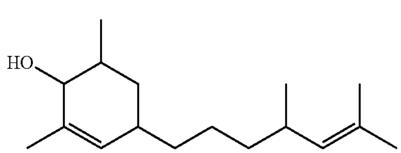 [SMILES: CC(C)=CC(C)CCCC1C=C(C)C(O)C(C)C1] |
| Example 29 | 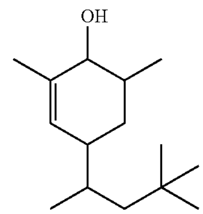 [SMILES: CC1=CC(C(C)CC(C)(C)C)CC(C)C1O] |
| Example 30 | 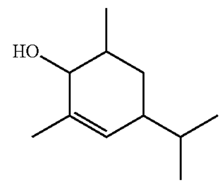 |
| Example 31 | 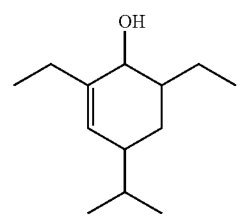 |
| Example 32 | 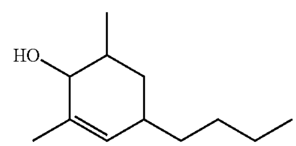 |
| Example 33 | 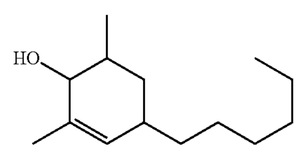 |
| Example 34 | 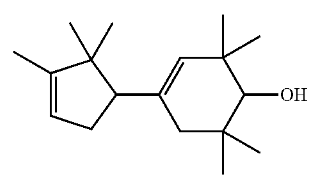 [SMILES: CC1=CCC(C2=CC(C)(C)C(O)C(C)(C)C2)C1(C)C] |
| Example 35 | 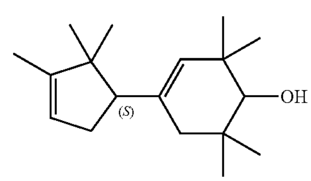 |
| Example 36 | 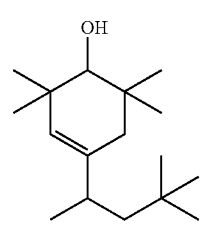 [SMILES: CC(CC(C)(C)C)C1=CC(C)(C)C(O)C(C)(C)C1] |

TABLE 1-continued

Structure of the synthesised compounds

| Example No. | Chemical structure |
|---|---|
| Example 37 | 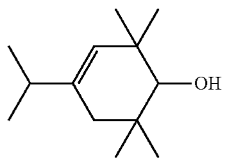 |
| Example 38 | 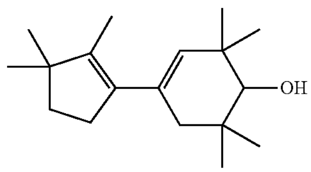 [SMILES: CC1=C(C2=CC(C)(C)C(O)C(C)(C)C2)CCC1(C)C] |
| Example 39 | 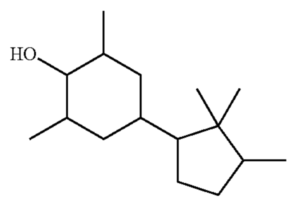 [SMILES: CC1CC(C2CCC(C)C2(C)C)CC(C)C1O] |
| Example 40 | 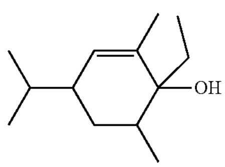 |
| Example 41 | 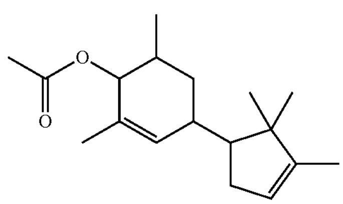 [SMILES: CC(=O)OC1C(C)=CC(C2CC=C(C)C2(C)C)CC1C] |
| Example 42 | 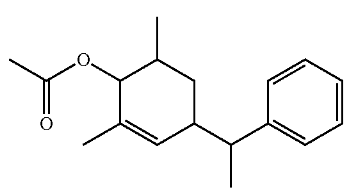 [SMILES: CC(=O)OC1C(C)=CC(C(C)c2ccccc2)CC1C] |
| Example 43 | 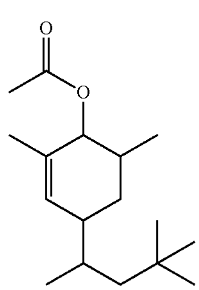 [SMILES: CC(=O)OC1C(C)=CC(C(C)CC(C)(C)C)CC1C] |
| Example 44 | 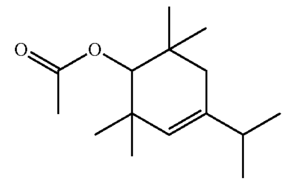 [SMILES: CC(=O)OC1C(C)(C)C=C(C(C)C)CC1(C)C] |
| Example 45 | 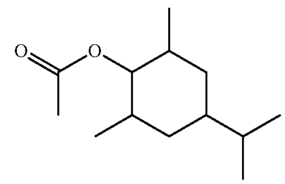 |
| Example 46 | 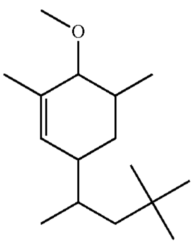 [SMILES: COC1C(C)=CC(C(C)CC(C)(C)C)CC1C] |

EXAMPLES

Synthesis of the Compounds Given by Way of Example in Table 1

Example 1

Preparation of 2,6-dimethyl-4-(2,2,3-trimethylcyclopent-3-enyl)cyclohex-2-enone 3-pentanone (129 g, 1.5 mol, 1.5 eq.) methylene-campholenaldehyde (prepared from 153 g, 1 mol, 1 eq. Campholenaldehyde and 1.1 eq. of formaldehyde) and potassium hydroxide (11.2 g, 0.2 mol, 0.2 eq.) in a water/ethanol mixture (300 ml/200 ml) are heated to 65° C. for one night. Once the reaction has finished, the reaction mixture is cooled and 0.2 eq. of acetic acid is added. The aqueous phase is extracted 3 times with methyl and t-butyl ether and the reunited organic phases are washed with brine, dried over magnesium sulphate and filtered. The solvents are evaporated and the raw product is purified by distillation to give 2,6-dimethyl-4-(2,2,3-trimethylcyclopent-3-enyl)cyclohex-2-enone in the form of a colourless oil with a yield of 57% over the 2 steps. It is a mixture of 4 observable isomers in a ratio 12:40:33:15.

B.p.: 105-107° C./0.5 torr

Olfactive profile: Woody (cedar), ambery, spicy (pepper)

NMR-$^1$H (CDCl$_3$, 200 MHz): δ(ppm) common protons 1.4-1.90 (m, 2H), 1.55-1.65 (m, 3H), 1.7-1.8 (m, 3H), 1.90-2.2 (m, 2H), 2.2-2.5 (m, 2H), 2.5-2.65 (m, 1H), 5.22 (m, 1H).

Majority isomers (characteristic protons): 0.96 (s, 3H), 1.09 (s, 3H), 1.13 (d, J=7.04 Hz), 6.64 (broad s, 1H)

Second majority isomer (characteristic protons): 0.92 (s, 3H), 1.06 (s, 3H), 1.12 (d, J=6.67 Hz), 6.66 (broad s, 1H)

Minority isomer (characteristic protons): 0.92 (s, 3H), 1.04 (s, 3H), 1.14 (d, J=5.68 Hz), 6.77 (broad s, 1H)

Second minority isomer (characteristic protons): 0.96 (s, 3H), 1.06 (s, 3H), 1.14 (d, J=5.68 Hz), 6.85 (br d, 1H)

NMR-$^{13}$C (CDCl$_3$, 50 MHz): δ(ppm)

Majority isomer: 12.52; 15.28; 16.43; 19.31; 27.03; 34.75; 35.43; 35.62; 38.23; 47.31; 52.0; 121.24; 133.99; 134.94; 148.82; 202.72.

Second majority isomer: 12.47; 15.67; 16.43; 19.93; 27.44; 33.64; 38.54; 39.28; 41.57; 47.22; 53.80; 121.24; 133.99; 134.94; 148.39; 202.29.

First minority isomer: 12.47; 15.67; 16.43; 20.08; 28.04; 33.95; 37.64; 38.85; 41.73; 46.99; 54.01; 121.19; 133.46; 134.51; 148.68; 202.32.

Second minority isomer: 12.52; 15.85; 16.35; 19.74; 27.24; 34.75; 35.50; 35.83; 37.69; 46.72; 53.18; 120.99; 134.51; 134.94; 148.73; 202.72.

Example 2

Preparation of 2,6-dimethyl-4-((R)-2,2,3-trimethyl-cyclopent-3-enyl)cyclohex-2-enone As described in example 1, 2,6-dimethyl-4-((R)-2,2,3-trimethylcyclopent-3-enyl)cyclohex-2-enone is prepared from R-(+)-campholenaldehyde with a yield of 49% over the 2 steps, it is a 12:36:35:17 mixture of observable isomers.

B.p.: 100° C./0.5 torr

Olfactive profile: nutty, anise

The analyses are in accordance with those obtained in example 1.

Example 3

Preparation of 2,6-dimethyl-4-((S)-2,2,3-trimethyl-cyclopent-3-enyl)cyclohex-2-enone As described in example 1, 2,6-dimethyl-4-((S)-2,2,3-trimethylcyclopent-3-enyl)cyclohex-2-enone is prepared from S-(−)-campholenaldehyde with a yield of 43% over the 2 steps, it is a 12:43:30:15 mixture of observable isomers.

B.p.: 101-102° C./0.5 torr

Olfactive profile: Roots, woody, vetiver, pepper

The analyses are in accordance with those obtained in example 1.

Example 4

Preparation of 2,6-diethyl-4-(2,2,3-trimethylcyclo-pent-3-enyl)cyclohex-2-enone 2,6-diethyl-4-(2,2,3-trimethylcyclopent-3-enyl)cyclohex-2-enone is obtained with a yield of 33%, according to example 1, from 5-heptanone and methylene-campholenaldehyde.

It is a 32:40:28 mixture of 3 isomers observable with a non-polar GPC column.

B.p.: 120° C./0.5 torr

Olfactive profile: Spicy, curry

NMR-$^1$H (CDCl$_3$, 200 MHz): δ(ppm) common protons 0.8-1.2 (m, 12H), 1.3-1.6 (m, 2H), 1.6 (m, 3H), 1.6-2.1 (m, 4H), 2.15 (q, J=7.4 Hz, 2H), 2.25-2.4 (m, 2H), 2.5-2.65 (m, 1H), 5.21 (m, 1H).

Majority isomers (characteristic protons—70%): 6.57 (br s, 1H)

Minority isomer (characteristic protons—15%): 6.72 (br s, 1H)

Minority isomer (characteristic protons—15%): 6.76 (br d, 1H)

NMR-$^{13}$C (CDCl$_3$, 50 MHz): δ(ppm)

2 Majority isomers (70% 50:50): 11.23 & 11.75 (CH$_3$), 12.43 & 12.49 (CH$_3$), 13.01 & 13.09 (CH$_3$), 19.44 & & 20.04 (CH$_3$), 22.20 & 22.79 & 22.94 (2CH$_2$), 27.10 & 27.52 (CH$_3$), 32.48 & 33.48 (CH$_2$), 34.54 & 35.52 (CH$_2$), 34.92 & 38.37 (CH), 45.74 & 48.04 (CH), 47.27 (C$^{IV}$), 52.67 & 53.98 (CH), 121.25 & 121.31 (CH), 139.67 & 140.85 (C$^{IV}$), 146.44 & 148.73 (CH), 148.34 & 148.36 (C$^{IV}$), 201.18 & 201.25 (C(O)).

2 minority isomers (30% 50:50, specific peaks): 11.23 & 11.57 (CH$_3$), 12.43 & 12.49 (CH$_3$), 12.83 & 12.88 (CH$_3$), 13.01 & 13.09 (CH$_3$), 19.85 & & 20.13 (CH$_3$), 22.23 & 22.61 & 22.71 & 22.79 (2CH$_2$), 27.38 & 28.03 (CH$_3$), 32.21 & 33.48 (CH$_2$), 33.97 & 34.03 (CH$_2$), 38.83 (CH), 45.02 & 48.18 (CH), 47.02 (C$^{IV}$), 53.48 & 54.30 (CH), 121.22 & 121.03 (CH), 146.58 & 146.67 (CH).

Example 5

Preparation of 2,6-dimethyl-4-(2,4,4-trimethylcyclo-pentyl)cyclohex-2-enone 2,6-dimethyl-4-(2,4,4-trimethylcyclopentyl)cyclohex-2-enone is obtained with a yield of 25%, according to example 1, from 3-pentanone and 2-(2,4,4-trimethylcyclopentyl) acrylaldehyde (prepared from 2,4,4-trimethylcyclopen-tanone).

It is a mixture of 5 isomers observable in a ratio 16:31:34:9:5:5.

B.p.: 72° C./0.3 torr

Olfactive profile: Dry woody, spicy, nutty.

NMR-$^1$H (CDCl$_3$, 200 MHz): 4 observed diastereoisomers δ(ppm) common protons 0.8-1.4 (m, 15H), 1.4-1.75 (m, 3H), 1.75 (m, 3H), 1.75-2.10 (m, 2H), 2.2-2.4 (m, 1H), 2.4-2.7 (m, 1H).

Majority isomers (characteristic protons—62%): 6.58 (m, 1H)

1st minority isomers (characteristic protons—18%): 6.49 (m, 1H)

2nd minority isomers (characteristic protons—15%): 6.59 (m, 1H)

3rd minority isomers (characteristic protons—5%): 6.67 (m, 1H)

NMR-$^{13}$C (CDCl$_3$, 50 MHz): 6-7 observed diastereoisomers

Majority isomers (characteristic peaks—41%): 202.59 (C(O)), 147.66 & 147.35 (CH), 135.33 & 134.24 (C$^{IV}$)

2nd Majority isomers (characteristic peaks—21%): 203.15 (C(O)), 149.71 (CH), 134.54 (C$^{IV}$)

1st minority isomers (characteristic peaks—16%): 203.09 (C(O)), 149.15 (CH), 133.28 (C$^{IV}$)

2nd minority isomers (characteristic peaks—12%): 202.49 (C(O)), 148.87 (CH), 134.54 & 134.49 (C$^{IV}$)

3rd minority isomers (characteristic peaks—6%): 202.79 (C(O)), 148.07 (CH), 133.59 (C$^{IV}$)

4th minority isomers (characteristic peaks—3%): 202.96 (C(O)), 147.98 (CH), 133.49 (C$^{IV}$)

Example 6

Preparation of 2,6-dimethyl-4-(1-phenyl-ethyl)cyclohex-2-enone 2,6-dimethyl-4-(1-phenyl-ethyl)cyclohex-2-enone is obtained with a yield of 54% during the 2 steps, according to example 1, from 3-pentanone and 2-methylene-3-phenylbutanal (prepared from 3-phenylbutanal).

It is a mixture of 4 observable isomers in a ratio 17:29:23:31.

B.p.: 115° C./0.5 torr

Olfactive profile: floral, balsamic, honey-like.

NMR-$^1$H (CDCl$_3$, 200 MHz): 4 observed diastereoisomers δ(ppm) common protons 0.95-1.15 (m, 3H), 1.22-1.35 (m, 3H), 1.25-2.10 (m, 2H), 1.62-1.80 (m, 3H), 2.15-2.90 (m, 3H), 7.12-7.35 (m, 5H).

Majority isomers (characteristic protons—31%): 6.65-6.70 (m, 1H)

Majority isomers (characteristic protons—29%): 6.75-6.80 (m, 1H)

Minority isomers (characteristic protons—23%): 6.37-6.42 (m, 1H)

Minority isomers (characteristic protons—17%): 6.27-6.35 (m, 1H)

NMR-$^{13}$C (CDCl$_3$, 75 MHz): 4 observed diastereoisomers

Majority isomers (characteristic peaks—31%): 202.23 (C(O)), 146.42 (CH), 135.43 ($C^{IV}$), 38.37, 36.88 (CH$_2$), 17.84, 16.35, 15.15.

2nd Majority isomers (characteristic peaks—29%): 202.52 (C(O)), 146.69 (CH), 134.44 ($C^{IV}$), 40.12, 34.33 (CH$_2$), 19.50, 16.47, 15.61.

Minority isomers (characteristic peaks—23%): 147.52 (CH), 134.95 ($C^{IV}$), 39.40, 35.33 (CH$_2$), 19.44, 16.22, 15.93.

2nd minority isomers (characteristic peaks—17%): 147.28 (CH), 133.73 ($C^{IV}$), 38.90, 33.39 (CH$_2$), 18.04, 15.15, 15.27.

Example 7

Preparation of 2,6-dimethyl-4-(6-methylhept-5-en-2-yl)cyclohex-2-enone 2,6-dimethyl-4-(6-methylhept-5-en-2-yl)cyclohex-2-enone is obtained with a yield of 51% during the 2 steps, according to example 1, from 3-pentanone and 2-methylene-citronnellal (prepared from citronellal).

It is a mixture of 4 observable isomers in a ratio 25:21:28:25.

B.p.: 109-110° C./0.7 Torr

Olfactive profile: floral, green, root, citronella, clean

NMR-$^1$H (CDCl$_3$, 200 MHz): 3 observed diastereoisomers δ(ppm) common protons 1.11 (d, J=6.78 Hz, 3H), 1.10-1.70 (m, 4H), 1.58 (s, 3H), 1.66 (s, 3H), 1.74 (s, 3H), 1.75-2.20 (m, 3H), 2.20-2.65 (m, 2H), 5.07 (br t, 1H), 6.45-6.60 (m, 1H).

Majority isomers (characteristic protons—28%): 0.91 (d, J=6.06 Hz, 3H)

Other isomers (characteristic protons): 0.87 (d, J=6.76 Hz, 3H, 2 isomers) & 0.82 (d, J=6.86 Hz, 3H)

NMR-$^{13}$C (CDCl$_3$, 75 MHz): 3 to 4 observed diastereoisomers 203.21 & 203.15 & 202.47 (C(O)), 149.36 & 148.89 & 148.16 & 147.86 (CH), 135.38 & 135.11 & 134.09 & 133.83 ($C^{IV}$), 131.54 ($C^{IV}$), 124.26 & 124.23 & 124.15 (CH), 42.11 & 41.66 & 41.5 & 41.43 (CH), 39.55 & 39.48 & 37.61 & 37.0 (CH), 36.37 & 36.04 & 36.0 (CH), 34.94 & 34.19 & 33.95 (CH$_2$), 33.63 & 33.03 & 32.58 & 30.87 (CH$_2$), 25.95 & 25.88 & 25.80 & 25.74 (CH$_2$), 25.65 (CH$_3$), 17.61 & 16.29 (CH$_3$), 16.74 & 16.36 (CH$_3$), 16.27 & 16.16 & 15.73 (CH$_3$), 15.97 & 15.91 & 15.32 & 15.29 (CH$_3$).

Example 8

Preparation of 4-(4,4-dimethylpentan-2-yl)-2,6-dimethylcyclohex-2-enone 4-(4,4-dimethylpentan-2-yl)-2,6-dimethylcyclohex-2-enone is obtained with a yield of 56% during the 2 steps, according to example 1, from 3-pentanone and 2-methylene-3,5,5-Trimethylhexanal (prepared from 3,5,5-Trimethylhexanal).

It is a mixture of 4 observable isomers in a ratio 23:17:30:30.

B.p.: 88-92° C./0.4 torr

Olfactive profile: woody, ambery, slightly sandalwood, hazelnut.

NMR-$^1$H (CDCl$_3$, 200 MHz): δ(ppm) 0.75-1.37 (m, 2H), 0.87-0.95 (m, 12H), 1.12 (d, J=7.2 Hz, 3H), 1.37-2.0 (m, 3H), 1.76 (m, 3H), 2.20-2.62 (m, 2H), 6.45-6.57 (m, 1H).

NMR-$^{13}$C (CDCl$_3$, 75 MHz): selected data 196.52 (C(O)), 149.06 & 148.64 & 148.60 & 148.20 (CH), 135.75 & 135.37 & 134.33 ($C^{IV}$), 48.46 & 47.97 & 47.92 & 47.74 (CH$_2$), 34.80 & 34.17 (CH$_2$), 32.40 & 31.67 & 31.02 ($C^{IV}$), 29.89 (3 CH$_3$).

Example 9 preparation of 4-isopropyl-2,6-dimethylcyclohex-2-enone 4-isopropyl-2,6-dimethylcyclohex-2-enone is obtained with a yield of 54% during the 2 steps, according to example 1, from 3-pentanone and 2-methylene-isovaleraldehyde (prepared from isovaleraldehyde).

It is a mixture of 2 observable isomers in a ratio 27:76.

B.p.: 62° C./1 torr

Olfactive profile: green, citrus, grapefruit peel.

NMR-$^1$H (CDCl$_3$, 200 MHz): common protons 1.30-1.55 (m, 1H), 1.62-1.82 (m, 1H), 1.76 (m, 3H), 1.82-2.0 (m, 1H), 2.20-2.41 (m, 1H).

Majority isomers (characteristic protons): δ(ppm) 0.89 (d, J=6.73 Hz, 3H), 0.92 (d, J=6.66 Hz, 3H), 1.12 (d, J=6.64 Hz, 3H), 2.20-2.41 (m, 1H), 6.55 (m, 1H).

Minority isomers: δ(ppm) 0.95 (d, J=6.72 Hz, 3H), 0.95 (d, J=6.72 Hz, 3H), 1.12 (d, J=7.2 Hz, 3H), 2.45-2.60 (m, 1H), 6.61 (m, 1H).

NMR-$^{13}$C (CDCl$_3$, 75 MHz):

Majority isomers: 202.60 (C(O)), 148.33 (CH), 135.18 ($C^{IV}$), 42.99 (CH), 41.50 (CH), 34.32 (CH$_2$), 31.81 (CH), 19.40 (CH$_3$), 19.01 (CH$_3$), 16.24 (CH$_3$), 15.32 (CH$_3$).

Minority isomers, specific peaks: 148.05 (CH), 133.89 ($C^{IV}$), 39.28 (CH), 39.01 (CH), 32.38 (CH$_2$), 31.46 (CH), 20.11 (CH$_3$), 20.06 (CH$_3$), 16.35 (CH$_3$), 15.94 (CH$_3$).

Example 10

Preparation of 4-butyl-2,6-diethylcyclohex-2-enone 4-butyl-2,6-diethylcyclohex-2-enone is obtained with a yield of 16% over the 2 steps, according to example 1, from 4-heptanone and 2-methylene-hexanal (prepared from hexanal).

It is a mixture of 2 observable isomers in a ratio 51:49.

B.p.: 115° C./0.5 torr

Olfactive profile: woody, hazelnut.

NMR-$^1$H (CDCl$_3$, 300 MHz): δ(ppm) 0.85-1.0 (m, 9H), 1.1-1.55 (m, 8H), 1.58-1.78 (m, 1H), 1.84-1.98 (m, 1H), 2.0-2.3 (m, 3H), 2.32-2.44 (m, 1H), 6.42-6.47 (m, 1H).

NMR-$^{13}$C (CDCl$_3$, 75 MHz): δ(ppm) 202.27 & 201.41 (C(O)), 147.62 & 147.0 (CH), 140.12 & 138.88 (C$^{IV}$), 47.78 & 46.25 (CH), 36.70 & 32.76 (CH), 35.61 & 34.38 (CH$_2$), 34.50 & 32.44 (CH$_2$), 29.29 & 28.72 (CH$_2$), 22.85 & 22.71 & 22.69 & 22.58 & 22.50 & 22.14 (3 CH$_2$), 13.94 (CH$_3$), 12.92 & 12.86 (CH$_3$), 11.79 & 11.11 (CH$_3$).

Example 11

Preparation of
2,6-dimethyl-4-propylcyclohex-2-enone 2,6-dimethyl-4-propylcyclohex-2-enone is obtained with a yield of 17% over the 2 steps, according to example 1, from 3-pentanone and 2-methylene-valeraldehyde (prepared from pentanal).

It is a mixture of 2 observable isomers in a ratio 54:46.

B.p.: 70° C./0.5 torr

Olfactive profile: grapefruit, very green, cocoa chocolate.

NMR-$^1$H (CDCl$_3$, 200 MHz):

δ(ppm) common protons 0.85-0.97 (m, 3H), 1.1 (d, J=7 Hz, 3H), 1.20-1.50 (m, 4H), 1.70-1.75 (m, 3H), 1.75-2.08 (m, 2H), 2.20-2.60 (m, 2H).

Majority isomers (characteristic proton): 6.54-6.59 (m, 1H)

Minority isomers (characteristic proton): 6.48-6.54 (m, 1H)

NMR-$^{13}$C (CDCl$_3$, 50 MHz):

Majority isomers: 202.98 (C(O)), 148.92 (CH), 133.30 (C$^{IV}$), 38.52, 38.28 (CH$_2$), 35.58 (CH$_2$), 32.99, 20.53 (CH$_2$), 16.23, 15.72, 14.08.

Minority isomers: 202.56 (C(O)), 149.56 (CH), 134.32 (C$^{IV}$), 41.41, 37.92 (CH$_2$), 36.57, 36.20 (CH$_2$), 19.64 (CH$_2$), 16.12, 15.22, 14.04.

Example 12

Preparation of
4-butyl-2,6-dimethylcyclohex-2-enone 4-butyl-2,6-dimethylcyclohex-2-enone is obtained with a yield of 40% over the 2 steps, according to example 1, from 3-pentanone and 2-methylene-hexanal (prepared from hexanal).

It is a mixture of 2 observable isomers in a ratio 57:43.

B.p.: 65° C./0.8 torr

Olfactive profile: Green, rhubarb, powerful, slightly lavender, mushroom.

NMR-$^1$H (CDCl$_3$, 200 MHz):

δ(ppm) common protons 0.85-0.95 (m, 3H), 1.1 (d, J=7 Hz, 3H), 1.18-1.62 (m, 6H), 1.70-1.75 (m, 3H), 1.76-2.08 (m, 2H), 2.20-2.60 (m, 2H).

Majority isomers (characteristic proton): 6.54-6.59 (m, 1H) Minority isomers (characteristic proton): 6.48-6.54 (m, 1H)

NMR-$^{13}$C (CDCl$_3$, 50 MHz):

Majority isomers: 202.93 (C(O)), 148.91 (CH), 133.27 (C$^{IV}$), 38.51, 35.61 (CH$_2$), 33.72 (CH$_2$), 33.23, 29.60 (CH$_2$), 22.72 (CH$_2$), 16.20, 15.71, 13.94.

Minority isomers: 202.50 (C(O)), 149.56 (CH), 134.31 (C$^{IV}$), 41.40, 38.30 (CH$_2$), 36.79, 35.40 (CH$_2$), 28.69 (CH$_2$), 22.67 (CH$_2$), 16.10, 15.20, 13.94.

Example 13

Preparation of
4-hexyl-2,6-dimethylcyclohex-2-enone 4-hexyl-2,6-dimethylcyclohex-2-enone is obtained with a yield of 35% over the 2 steps, according to example 1, from 3-pentanone and 2-methylene-octanal (prepared from octanal).

It is a mixture of 2 observable isomers in a ratio 48:52.

B.p.: 105° C./0.5 torr

Olfactive profile: aldehyde, fresh and clean linen, household soap, hay-like.

NMR-$^1$H (CDCl$_3$, 200 MHz):

δ(ppm) common protons 0.83-1.04 (m, 3H), 1.12 (d, J=6.8 Hz, 3H), 1.22-1.50 (m, 10H), 1.73-1.78 (m, 3H), 1.75-2.10 (m, 2H), 2.10-2.65 (m, 2H).

Minority isomers (characteristic proton): 6.54-6.59 (m, 1H)

Majority isomers (characteristic proton): 6.50-6.55 (m, 1H)

NMR-$^{13}$C (CDCl$_3$, 50 MHz):

Minority isomers: 198.20 (C(O)), 148.95 (CH), 38.59, 38.36 (CH$_2$), 35.68 (CH$_2$), 33.31, 31.78 (CH$_2$), 29.38 (CH$_2$), 27.44 (CH$_2$), 22.62 (CH$_2$), 16.27, 15.78, 14.06.

Majority isomers: 196.54 (C(O)), 149.60 (CH), 134.38 (C$^{IV}$), 41.47, 36.88, 35.78 (CH$_2$), 34.10 (CH$_2$), 31.78 (CH$_2$), 29.33 (CH$_2$), 26.52 (CH$_2$), 22.62 (CH$_2$), 16.17, 15.29, 14.06.

Example 14

Preparation of (R)-2,2,6,6-tetramethyl-4-(2,2,3-trimethylcyclopent-3-enyl)cyclohex-3-enone To a solution in THF of 2,6-dimethyl-4-((R)-2,2,3-trimethylcyclopent-3-enyl)cyclohex-2-enone (obtained according to example 2) are added 1.1 molar equivalent of potassium t-butylate. After 2 hours of agitation at ambient temperature, 1.1 molar equivalent of methyl iodide are added drop by drop to the reaction mixture. 1.1 molar equivalent of potassium t-butylate are also then added and the reaction mixture is heated to 40° C. for 2 hours, then a new 1.1 molar of methyl iodide is added. After agitation at 40° C. for one night, the reaction mixture is diluted with methyl and t-butyl ether and poured into a 10% aqueous HCl solution. The aqueous phase is extracted twice with methyl and t-butyl ether and the reunited organic phases are washed with a saturated aqueous solution of sodium bicarbonate. The organic phase is dried over magnesium sulphate, filtered and the solvents are evaporated. The raw product thus obtained is purified by distillation to give (R)-2,2,6,6-tetramethyl-4-(2,2,3-trimethylcyclopent-3-enyl)cyclohex-3-enone in the form of a colourless oil with a yield of 64%.

B.p.: 93° C./0.5 torr

Olfactive profile: Dusty, musty

IR (film, cm$^{-1}$): 564m, 581m, 797m, 857w, 997w, 1013w, 1047m, 1360m, 1381m, 1466 m, 1706s, 2866w, 2927m, 2958m.

NMR-$^1$H (CDCl$_3$, 200 MHz): δ(ppm) 0.75 (s, 3H), 1.05 (s, 3H), 1.09 (s, 3H), 1.11 (s, 3H), 1.11 (s, 3H), 1.13 (s, 3H), 1.58 (m, 3H), 2.10-2.40 (m, 2H), 2.22 (q, J=16.54 Hz, 2H), 2.50 (t, J=8.22 Hz, 1H), 5.22-5.29 (m, 1H), 5.39-5.43 (m, 1H).

NMR-$^{13}$C (CDCl$_3$, 75 MHz): δ(ppm) 12.67 (CH$_3$), 21.10 (CH$_3$), 25.40 (CH$_3$), 25.61 (CH$_3$), 26.77 (CH$_3$), 27.19 (CH$_3$), 27.21 (CH$_3$), 33.01 (CH$_2$), 41.96 (CH$_2$), 43.08 (C$^{IV}$), 43.76 (C$^{IV}$), 48.17 (C$^{IV}$), 57.83 (CH), 121.36 (CH), 131.70 (CH), 134.91 (C$^{IV}$), 147.43 (C$^{IV}$), 219.92 (C(O)).

Example 15

Preparation of (S)-2,2,6,6-tetramethyl-4-(2,2,3-trimethylcyclopent-3-enyl)cyclohex-3-enone (S)-2,2,6,6-tetramethyl-4-(2,2,3-trimethylcyclopent-3-enyl)cyclohex-3-enone is obtained with a yield of 46% according to example 14 from 2,6-dimethyl-4-((S)-2,2,3-trimethylcyclopent-3-enyl)cyclohex-2-enone (obtained in example 3).

B.p.: 92° C./0.5 torr

Olfactive profile: Woody, fresh, musty

NMR-$^1$H (CDCl$_3$, 200 MHz): δ(ppm) 0.76 (s, 3H), 1.05 (s, 3H), 1.10 (s, 3H), 1.12 (s, 6H), 1.14 (s, 3H), 1.59 (m, 3H), 2.10-2.40 (m, 2H), 2.22 (q, J=16.53 Hz, 2H), 2.51 (t, J=8.23 Hz, 1H), 5.23-5.30 (m, 1H), 5.40-5.44 (m, 1H).

NMR-$^{13}$C (CDCl$_3$, 50 MHz): δ(ppm) 12.66 (CH$_3$), 21.08 (CH$_3$), 25.39 (CH$_3$), 25.60 (CH$_3$), 26.75 (CH$_3$), 27.17 (CH$_3$), 27.19 (CH$_3$), 33.00 (CH$_2$), 41.94 (CH$_2$), 43.06 (C$^{IV}$), 43.74 (C$^{IV}$), 48.16 (C$^{IV}$), 57.81 (CH), 121.35 (CH), 131.68 (CH), 134.89 (C$^{IV}$), 147.41 (C$^{IV}$), 219.90 (C(O)).

Example 16

Preparation of 4-(4,4-dimethyl pentan-2-yl)-2,2,6,6-tetramethylcyclohex-3-enone 4-(4,4-dimethylpentan-2-yl)-2,2,6,6-tetramethylcyclohex-3-enone is obtained with a yield of 30% according to example 14 from 4-(4,4-dimethylpentan-2-yl)-2,6-dimethylcyclohex-2-enone (obtained in example 9).

B.p.: 75° C./0.4 torr

Olfactive profile: Woody, peppery, slightly fruity and ambery.

NMR-$^1$H (CDCl$_3$, 300 MHz): δ(ppm) 0.89 (s, 9H), 0.9-1.35 (m, 1H), 1.01 (d, J=6.93 Hz, 3H), 1.07 (s, 3H), 1.08 (s, 3H), 1.10 (s, 3H), 1.12 (s, 3H), 1.36-1.46 (m, 1H), 2.04-2.2 (m, 2H), 2.23-2.38 (m, 1H), 5.30 (s, 1H).

NMR-$^{13}$C (CDCl$_3$, 75 MHz): δ(ppm) 220.10 (C(O)), 140.23 (C$^{IV}$), 128.24 (CH), 48.04 (CH$_2$), 43.44 (C$^{IV}$), 42.84 (C$^{IV}$), 38.16 (CH$_2$), 37.18 (CH), 31.22 (C$^{IV}$), 29.88 (3 CH$_3$), 27.24 (CH$_3$), 26.46 (CH$_3$), 25.52, 25.43, 22.43.

Example 17

Preparation of 4-isopropyl-2,2,6,6-tetramethylcyclohex-3-enone 4-isopropyl-2,2,6,6-tetramethylcyclohex-3-enone is obtained with a yield of 46% according to example 14 from 4-isopropyl-2,6-dimethylcyclohex-2-enone (obtained in example 10).

B.p.: 86-87° C./9 torr

Olfactive profile: camphor, earthy, woody, animal.

NMR-$^1$H (CDCl$_3$, 200 MHz): δ(ppm) 1.01 (d, J=6.81 Hz, 1H), 1.09-1.12 (m, 12H), 2.14 (s, 2H), 2.25 (hept, J=13.80 Hz, 1H), 5.28 (s, 1H).

NMR-$^{13}$C (CDCl$_3$, 50 MHz): δ(ppm) 215.8 (C(O)), 140.12 (C$^{IV}$), 127.13 (CH), 43.41 (C$^{IV}$), 42.89 (C$^{IV}$), 39.11 (CH$_2$), 34.72 (CH), 27.16 (2CH$_3$), 25.42 (2CH$_3$), 20.90 (2CH$_3$).

Example 18

Preparation of 4-isopropyl-2,6-dimethyl-2,6-dipropylcyclohex-3-enone 4-isopropyl-2,6-dimethyl-2,6-dipropylcyclohex-3-enone is obtained with a yield of 39% according to example 14 from 4-isopropyl-2,6-dimethylcyclohex-2-enone (obtained in example 10) and 1-bromopropane.

B.p.: 75° C./0.5 torr

Olfactive profile: Weak head, sweat, dusty, dry woody, slightly cassis.

NMR-$^1$H (CDCl$_3$, 200 MHz): δ(ppm) 0.83 (t, J=6.81 Hz, 6H), 0.97-1.07 (m, 12H), 1.07-1.37 (m, 5H), 1.37-1.55 (m, 2H), 1.65-2.15 (m, 3H), 2.28 (hept, J=13.70 Hz, 1H), 5.20 (s, 1H).

NMR-$^{13}$C (CDCl$_3$, 50 MHz): δ(ppm) 217.8 (C(O)), 141.33 (C$^{IV}$), 125.40 (CH), 47.61 (C$^{IV}$), 46.43 (C$^{IV}$), 43.86 (CH$_2$), 40.0 (CH$_2$), 37.20 (CH$_2$), 35.08 (CH), 26.81 (CH$_3$), 22.55 (CH$_3$), 21.14 (CH$_3$), 21.03 (CH$_3$), 18.52 (CH$_2$), 17.31 (CH$_2$), 14.60 (CH$_3$), 14.53 (CH$_3$).

Example 19

Preparation of 2,2,6,6-tetramethyl-4-((1R)-2,2,3-trimethylcyclopentyl)cyclohex-3-enone A 1M solution in toluene of (S)-2,2,6,6-tetramethyl-4-(2,2,3-trimethylcyclopent-3-enyl)cyclohex-3-enone (obtained in example 15) with 5% by weight of 5% palladium on carbon is hydrogenated (p(H$_2$)=20 bars) at ambient temperature. Once the reaction has finished (GPC monitoring), the mixture is filtered over a Celite® cake and the solvents are evaporated. The raw oil thus obtained is distilled to give 2,2,6,6-tetramethyl-4-((1R)-2,2,3-trimethylcyclopentyl)cyclohex-3-enone and 2,2,6,6-tetramethyl-4-(2,3,3-trimethylcyclopent-1-enyl)cyclohexanone (72:28) with a yield of 78%.

B.p.: 95° C./0.6 torr

Olfactive profile: Animal, cresol, phenol 2,2,6,6-tetramethyl-4-((1R)-2,2,3 trimethylcyclopentyl)cyclohex-3-enone NMR-$^1$H (CDCl$_3$, 300 MHz): δ(ppm)
0.54 (s, 3H), 0.83 (d, J=6.78 Hz, 3H), 0.92 (s, 3H), 1.09 (s, 3H), 1.11 (s, 6H), 1.13 (s, 3H), 1.15-1.30 (m, 1H), 1.50-1.85 (m, 4H), 2.07-2.22 (m, 1H), 2.30 (d, J=15.97 Hz, 1H), 2.12 (d, J=16.45 Hz, 1H), 5.35 (m, 1H).

NMR-$^{13}$C (CDCl$_3$, 75 MHz): δ(ppm) 220.14 (C(CO)), 134.45 (C$^{IV}$), 131.87 (CH), 58.07 (CH), 45.17 (CH), 43.79 (2 C$^{IV}$), 43.25 (C$^{IV}$), 42.14 (CH$_2$), 29.72 (CH$_2$), 27.25 (CH$_3$), 27.18 (CH$_3$), 26.60 (CH$_3$), 25.57 (CH$_3$), 25.46 (CH$_2$), 25.38 (CH$_3$), 15.68 (CH$_3$), 14.11 (CH$_3$).

2,2,6,6-Tetramethyl-4-(2,3,3-trimethylcyclopent-1-enyl)cyclohexanone

NMR-$^1$H (CDCl$_3$, 300 MHz): δ(ppm)
0.88 (d, J=6.69 Hz, 3H), 0.90 (s, 3H), 1.06 (s, 3H), 1.08 (s, 3H), 1.09 (s, 3H), 1.11 (s, 3H), 1.19 (s, 3H), 1.55-1.85 (m, 2H), 2.07-2.29 (m, 2H), 2.22 (d, J=16.67 Hz, 1H), 2.34 (d, J=16.02 Hz, 1H), 2.58-2.64 (m, 2H), 5.35 (m, 1H).

NMR-$^{13}$C (CDCl$_3$, 75 MHz): δ(ppm) 220.55 (C(CO)), 146.79 (C$^{IV}$), 122.07 (C$^{IV}$), 46.91 (CH), 44.16 (CH), 43.91 (C$^{IV}$), 43.49 (C$^{IV}$), 42.90 (CH$_2$), 39.82 (CH$_2$), 30.77 (CH$_2$), 30.67 (CH₂), 27.09 (CH₃), 26.99 (CH₃), 26.91 (CH₃), 26.85 (CH₃), 26.77 (CH₃), 20.53 (CH₃), 13.48 (CH₃).

Example 20

Preparation of 4-(4,4-dimethylpentan-2-yl)-2,6-dimethylcyclohexanone 4-(4,4-dimethylpentan-2-yl)-2,6-dimethylcyclohexanone is obtained with a yield of 81% according to example 19 from 4-(4,4-dimethylpentan-2-yl)-2,6-dimethylcyclohex-2-enone (obtained in example 9).

It is a mixture of 2 main isomers (91%) in a ratio 29:71.
B.p.=76° C./0.4 torr
Olfactive profile: Woody, ambery, dusty, slightly flowery.
NMR-$^1$H (CDCl₃, 300 MHz): common protons δ(ppm) 0.85-0.94 (m, 12H), 0.94-1.03 (m, 6H), 1.04-1.41 (m, 4H), 1.41-1.55 (m, 1H), 1.6-2.15 (m, 3H).
Majority isomers (characteristic peak): 2.33-2.48 (m, 2H).
Minority isomers (characteristic peak): 2.48-2.62 (m, 2H).
NMR-$^{13}$C (CDCl₃, 75 MHz):
Majority isomers: δ(ppm) 214.81 (C(CO)), 48.54 (CH₂), 44.41 (CH), 44.30 (CH), 43.70 (CH), 40.13 (CH₂), 38.66 (CH₂), 32.76 (CH), 30.95 ($C^{IV}$), 29.84 (3 CH₃), 19.09 (CH₃), 14.63 (CH₃), 14.59 (CH₃).

Example 21

Preparation of 2,6-diethyl-4-isopropyl-2,6-dimethylcyclohexanone 2,6-diethyl-4-isopropyl-2,6-dimethylcyclohexanone is obtained with a yield of 40% over 2 steps (hydrogenation according to example 19, followed by alkylation with bromoethane according to example 14), from cyclohexenone obtained in example 10.

It is a mixture of observable stereoisomers in a ratio 6:16:57:21.
B.p.=63-65° C./0.4 torr
Olfactive profile: Woody, slightly nutty, hazelnut, plastic, slightly rosey.
NMR-$^1$H (CDCl₃, 300 MHz): common protons δ(ppm) 0.71-0.83 (m, 6H), 0.84-0.94 (m, 6H), 1.11-1.3 (m, 2H), 1.3-1.58 (m, 4H), 1.58-1.95 (m, 4H).
Majority isomers (characteristic peak): 0.97 (s, 6H).
Minority isomers (characteristic peak): 0.96 & 1.06 & 1.07 (s, 3H).
NMR-$^{13}$C (CDCl₃, 75 MHz): 4 observed stereoisomers including 3 majority stereoisomers
Majority isomers: δ(ppm) 220.09 & 219.40 (C(CO)), 41.45 & 40.70 & 39.31 (CH₂), 39.15 ($C^{IV}$), 34.18 (2C) & 34.07 (CH), 33.16 & 32.17 & 31.25 (CH₂), 32.35 (2C) & 32.21 (CH), 26.37 & 24.65 & 24.41 (CH₃), 19.84 & 19.72 & 19.62 (CH₃), 8.75 & 8.38 & 8.27 (CH₃).
Minority isomers (characteristic peaks): δ(ppm) 38.62 (CH₂), 34.28 (CH), 33.08 (CH₂), 32.27 (CH), 27.57 (CH₃), 19.72 (CH₃), 8.71 (CH₃).

Example 22

Preparation of 2,6-dimethyl-4-(2,2,3-trimethylcyclopent-3-enyl)cyclohex-2-enol

To a suspension of lithium aluminium hydride (5.8 g, 0.151 mol, 1.3 eq. H—) in 500 ml of diethyl ether, is added drop by drop at 20-25° C. 2,6-dimethyl-4-(2,2,3-trimethylcyclopent-3-enyl)cyclohex-2-enone (108 g, 0.465 mol, 1 eq., obtained in example 1). Once the reaction has finished, a 10% aqueous HCl solution is added drop by drop to precipitate the alumina.

After filtration and drying over magnesium sulphate, the solvents are evaporated and the raw product is purified by distillation to give 2,6-dimethyl-4-(2,2,3-trimethylcyclopent-3-enyl) cyclohex-2-enol in the form of a colourless oil with a yield of 76%. It consists in a mixture of 5 observable main isomers in a ratio 6:24:23:32:15 with a non-polar GPC column.

B.p.: 108-110° C./0.46 torr
Olfactive profile: Sandalwood, sweet, milky
NMR-$^1$H (CDCl₃, 200 MHz): δ(ppm) common protons 0.88-0.93 (m, 3H), 0.93-1.15 (m, 6H), 1.42-1.72 (m, 6H), 1.72-1.81 (m, 3H), 1.81-2.07 (m, 2H), 2.11-2.4 (m, 2H), 5.21 (m, 1H).
Majority isomers (characteristic protons, 32%): 3.65 (m, 1H), 5.43 (m, 1H)
2$^{nd}$ Majority isomers (characteristic protons, 2× 20%): 3.55 (d, J=4.59 Hz, 1H) & 3.78 (d, J=3.57 Hz, 1H), 5.47-5.52 (m, 1H).
Minority isomers (characteristic protons, 15%): 3.64 (m, 1H), 5.63 (m, 1H) Other minority isomers (characteristic protons, 6% & 7%): 3.72 & 3.90 (m, 1H), 5.66-5.74 (m, 1H)
NMR-$^{13}$C (CDCl₃, 75 MHz): δ(ppm)
Majority isomers (32%): 148.47 ($C^{IV}$), 136.13 ($C^{IV}$), 128.59 (CH), 121.42 (CH), 76.75 (CHOH), 54.76 (CH), 47.10 ($C^{IV}$), 38.37 (CH), 38.09 (CH2), 37.72 (CH), 33.76 (CH₂), 19.71 (CH₃), 19.51 (CH₃), 19.37 (CH₃), 19.26 (CH₃), 12.48 (CH₃).
Minority isomers (characteristic peaks, 55%): 148.54 & 148.48 & 148.42 ($C^{IV}$), 135.79 & 134.97 & 134.14 ($C^{IV}$), 129.17 & 129.08 & 128.94 (CH), 121.42 (2C) & 121.25 (CH), 76.75 & 74.79 & 71.61 (CHOH), 54.97 & 53.71 & 52.55 (CH), 47.14 & 47.08 & 46.90 ($C^{IV}$).
Other minority isomers (characteristic peaks, 6% & 7%): 149.11 & 148.89 ($C^{IV}$), 134.56 & 133.98 ($C^{IV}$), 129.13 & 129.06 (CH), 121.10 & 121.0 (CH), 75.28 & 71.43 (CHOH), 54.48 & 53.53 (CH), 46.77 & 46.62 ($C^{IV}$).

Example 23

Preparation of 2,6-dimethyl-4-((R)-2,2,3-trimethylcyclopent-3-enyl)cyclohex-2-enol 2,6-dimethyl-4-((R)-2,2,3-trimethylcyclopent-3-enyl)cyclohex-2-enol is obtained with a yield of 69%, according to example 22, from 2,6-dimethyl-4-(2,2,3-trimethylcyclopent-3-enyl)cyclohex-2-enone (obtained in example 2).

It is a mixture of 4 observable main isomers in a ratio 11:15:41:33 with a non-polar GPC column.
B.p.: 100-102° C./0.5 torr
Olfactive profile: Sandalwood, slightly green
The analyses are in accordance with those obtained in example 24.

Example 24

Preparation of 2,6-dimethyl-4-((S)-2,2,3-trimethylcyclopent-3-enyl)cyclohex-2-enol 2,6-dimethyl-4-((S)-2,2,3-trimethylcyclopent-3-enyl)cyclohex-2-enol is obtained with a yield of 66%, according to example 22, from 2,6-dimethyl-4-(2,2,3-trimethylcyclopent-3-enyl)cyclohex-2-enone (obtained in example 3). It consists in a mixture of 4 observable main isomers in a ratio of 10:20:33:37 with a non-polar GPC column, 7 observable isomers in a ratio 18:6:2:15:27:24:8 with a GC polar GPC column.

B.p.: 100-102° C./0.5 torr

Olfactive profile: Sandalwood, creamy, gourmand, hazelnut, slightly spicy, leathery IR (film, cm$^{-1}$): 564w, 580w, 880m, 1046s, 1088m, 1378w, 2875w, 2971w, 3318 w br.

NMR-$^1$H (CDCl$_3$, 200 MHz): δ(ppm) common protons 0.85-0.92 (m, 3H), 0.92-1.2 (m, 6H), 1.58 (m, 6H), 1.6-1.85 (m, 4H), 1.85-2.1 (m, 1H), 2.1-2.4 (m, 2H), 5.21 (m, 1H).

Isomer 27% (characteristic protons): 3.64 (d, J=6.50 Hz, 1H), 5.39-5.45 (m, 1H)

Isomer 24% (characteristic protons): 3.55 (d, J=4.83 Hz, 1H), 5.45-5.54 (m, 1H)

Isomer 18% (characteristic protons): 3.78 (d, J=3.89 Hz, 1H), 5.45-5.54 (m, 1H)

Isomer 15% (characteristic protons): 3.64 (d, J=6.50 Hz, 1H), 5.65-5.75 (m, 1H)

Minority isomer (8%, characteristic protons): 3.74 (d, J=3.98 Hz, 1H), 5.60-5.66 (m, 1H)

Minority isomer (6%, characteristic protons): 3.91 (t, J=6.67 Hz, 1H), 5.60-5.66 (m, 1H)

Minority isomer 2% (characteristic protons): 3.78 (d, J=3.89 Hz, 1H), 5.45-5.54 (m, 1H)

NMR-$^{13}$C (CDCl$_3$, 50 MHz): δ(ppm)

Majority isomers: 12.52, 15.28, 16.43, 19.31, 27.03, 34.75, 35.43, 35.62, 38.23, 47.31, 52.0, 121.24, 133.99, 134.94, 148.82, 202.72.

2nd Majority isomers: 12.47, 15.67, 16.43, 19.93, 27.44, 33.64, 38.54, 39.28, 41.57, 47.22, 53.80, 121.24, 133.99, 134.94, 148.39, 202.29.

Minority isomers: 12.47, 15.67, 16.43, 20.08, 28.04, 33.95, 37.64, 38.85, 41.73, 46.99, 54.01, 121.19, 133.46, 134.51, 148.68, 202.32.

2$^{nd}$ Minority isomers: 12.52, 15.85, 16.35, 19.74, 27.24, 34.75, 35.50, 35.83, 37.69, 46.72, 53.18, 120.99, 134.51, 134.94, 148.73, 202.72.

Example 25

Preparation of 2,6-diethyl-4-(2,2,3-trimethylcyclopent-3-enyl)cyclohex-2-enol 2,6-diethyl-4-(2,2,3-trimethylcyclopent-3-enyl)cyclohex-2-enol is obtained with a yield of 67%, according to example 22, from 2,6-diethyl-4-(2,2,3-trimethylcyclopent-3-enyl)cyclohex-2-enone (obtained in example 4).

It is a mixture of 4 isomers in a ratio 4:17:32:47.

B.p.: 120° C./0.45 torr

Olfactive profile: Sandalwood, weaker than example 11

NMR-$^1$H (CDCl$_3$, 200 MHz): δ(ppm) common protons 0.89-0.94 (m, 3H), 0.94-1.0 (m, 3H), 1.0-1.05 (m, 3H), 1.05-1.16 (m, 3H), 1.16-1.58 (m, 4H), 1.56-1.61 (m, 3H), 1.61-2.12 (m, 4H), 2.12-2.37 (m, 3H).

Isomers 47% (characteristic protons): 3.85 (d, J=9.32 Hz, 1H), 5.41-5.45 (m, 1H, 39%) & 5.63 (d, J=4.76 Hz, 1H, 8%)

Isomers 32% (characteristic protons): 3.8 (d, J=9.4 Hz, 1H), 5.51 & 5.63 & 5.67 (m, 1H, 11% & 14% & 7%)

Isomers 17% (characteristic protons): 3.65-3.73 (m, 1H), 5.48 (m, 1H)

Isomers 4% (characteristic protons): 3.8 (d, J=9.4 Hz, 1H), 5.48 (m, 1H)

NMR-$^{13}$C (CDCl$_3$, 50 MHz): δ(ppm)

Majority isomers: 148.39 (C$^{IV}$), 141.89 (C$^{IV}$), 126.81 (CH), 121.52 (CH), 68.61 (CHOH), 54.89 (CH), 47.20 (C1V), 44.99 (CH), 37.54 (CH), 33.98 (CH$_2$), 33.55 (CH$_2$), 27.49 (CH$_3$), 25.75 (CH$_2$), 25.52 (CH$_2$), 19.91 (CH$_3$), 12.78 (CH$_3$), 12.47 (CH$_3$), 11.12 (CH$_3$).

2$^{nd}$ Majority isomers (specific peaks): 127.95 (CH), 121.47 (CH), 73.39 (CHOH)

Minority isomers (specific peaks): 127.55 & 127.08 (CH), 121.31 & 121.03 (CH), 73.51 (CHOH)

Example 26

Preparation of 2,6-dimethyl-4-(2,4,4-trimethylcyclopentyl)cyclohex-2-enol 2,6-dimethyl-4-(2,4,4-trimethylcyclopentyl)cyclohex-2-enol is obtained with a yield of 40%, according to example 22, from 2,6-dimethyl-4-(2,4,4-trimethylcyclopentyl)cyclohex-2-enone (obtained in example 5).

The raw product was purified by chromatography on a silicon column, the expected alcohol consists in a mixture of 2 main isomers (83%) in a ratio of 19:81.

Olfactive profile: Tobacco, smoky

NMR-$^1$H (CDCl$_3$, 200 MHz): 3 observable isomers (50:30:20)

δ(ppm) common protons 0.80-0.97 (m, 6H), 0.97-1.02 (m, 6H), 1.02-1.20 (m, 4H), 1.20-1.75 (m, 8H), 1.72-1.8 (m, 3H), 1.8-2.0 (m, 1H), 2.0-2.35 (m, 1H).

1st Isomers (characteristic protons): 3.55-3.67 (m, 1H), 5.40-5.46 (m, 1H).

2nd Isomers (characteristic protons): 3.77-3.82 (m, 1H), 5.33-5.34 (m, 1H).

3rd Isomers (characteristic protons): 3.50-3.55 (m, 1H), 5.26-5.32 (m, 1H).

NMR-$^{13}$C (CDCl$_3$, 50 MHz): 6 observable isomers

1st Isomers (characteristic peaks): 136.49 (C$^{IV}$), 127.49 (CH), 71.90 (CHOH), 51.90 (CH), 50.64 (CH$_2$), 44.08 (CH$_2$), 38.19 (CH), 37.07 (CH$_2$).

2nd Isomers (characteristic peaks): 135.45 (C$^{IV}$), 129.76 (CH), 77.14 (CHOH), 51.78 (CH), 50.56 (CH$_2$), 45.81 (CH$_2$), 38.71 (CH), 30.57 (CH$_2$).

3rd Isomers (characteristic peaks): 135.41 (C$^{IV}$), 127.10 (CH), 76.94 (CHOH), 51.69 (CH), 50.56 (CH$_2$), 43.52 (CH$_2$), 38.25 (CH), 32.54 (CH$_2$).

Example 27

Preparation of 2,6-dimethyl-4-(6-methylhept-5-en-2-yl)cyclohex-2-enol 2,6-dimethyl-4-(6-methylhept-5-en-2-yl)cyclohex-2-enol is obtained with a yield of 56%, according to example 22, from 2,6-dimethyl-4-(6-methylhept-5-en-2-yl)cyclohex-2-enone (obtained in example 7).

It is a mixture of isomers including 1 main isomer (75%).

B.p.: 104° C./0.8 torr

Olfactive profile: Rosey, citronellol, slightly woody, plastic.

NMR-$^1$H (CDCl$_3$, 200 MHz): 2 observable isomers (70:30)

δ(ppm) common protons 0.75-0.85 (m, 3H), 0.95-1.20 (m, 1H), 1.20-1.57 (m, 5H), 1.59 (s, 3H), 1.68 (s, 3H), 1.82-2.22 (m, 3H), 5.03-5.15 (m, 1H).

1st Isomers (characteristic protons): 1.08 (d, J=6.38 Hz, 3H), 1.72-1.76 (m, 3H), 3.63 (broad d, J=8.55 Hz, 1H), 5.26-5.34 (m, 1H).

2nd Isomers (characteristic protons): 0.97 (d, J=6.88 Hz, 3H), 1.76-1.80 (m, 3H), 3.88 (broad t, 1H), 5.36-5.44 (m, 1H).

NMR-$^{13}$C (CDCl$_3$, 50 MHz): 4 observable isomers (2 majority isomers)

δ(ppm) common peaks 131.18 (C$^{IV}$), 124.82 & 124.77 (CH), 25.69 (CH$_3$), 19.41 & 19.38 & 19.34.

1st Isomers (characteristic peaks): 136.39 & 136.04 (C$^{IV}$), 129.35 & 128.15 (CH), 77.11 & 77.06 (CHOH), 41.33 & 40.78 (CH), 38.55 & 38.41 (CH), 36.71 & 36.69 (CH), 34.02 & 33.77 (CH$_2$), 33.50 & 31.95 (CH$_2$), 26.12 & 26.02 (CH$_2$), 19.25 & 17.62 (CH$_3$), 16.24 & 15.21 (CH$_3$).

2nd Isomers (characteristic peaks): 135.41 & 135.10 (C$^{IV}$), 128.25 & 127.32 (CH), 71.92 (2 CHOH), 38.27 & 37.80 (CH), 36.83 & 36.59 (CH), 34.53 & 34.44 (CH$_2$), 31.79 & 31.73 (CH), 28.70 & 27.41 (CH$_2$), 25.89 (2× CH$_2$), 20.87 & 20.76 (CH$_3$), 17.09 & 16.70 (CH$_3$), 15.21 & 15.08 (CH$_3$).

Example 28

Preparation of 4-(4,6-dimethylhept-5-enyl)-2,6-dimethylcyclohex-2-enol 4-(4,6-dimethylhept-5-enyl)-2,6-dimethylcyclohex-2-enol is obtained with a yield of 70%, according to example 22, from 4-(4,6-dimethylhept-5-enyl)-2,6-dimethylcyclohex-2-enone (obtained, according to example 1, with a yield of 16% during the 2 steps, from 3-pentanone and 5,7-dimethyl-2-methylene-oct-6-enal (prepared from 5,7-dimethyl-oct-6-enal)).

The raw product is purified by chromatography on a silica column, the expected alcohol consists in a mixture of isomers including 2 main isomers (74%) in a ratio of 32:68.

Olfactive profile: Weak head, slightly soapy, fruity, then woody, dusty.

NMR-$^1$H (CDCl$_3$, 300 MHz): 3 observable isomers (60:27:13)

δ(ppm) common protons 0.89 (d, J=6.60 Hz, 3H), 0.89-0.97 (m, 1H), 1.14-1.47 (m, 6H), 1.60 (s, 3H), 1.68 (s, 3H), 1.72-1.79 (m, 3H), 1.94-2.14 (m, 1H) 0.75-0.85 (m, 3H), 0.95-1.20 (m, 1H), 1.20-1.57 (m, 5H), 1.59 (s, 3H), 1.68 (s, 3H), 1.82-2.22 (m, 3H), 5.03-5.15 (m, 1H).

Majority isomers (characteristic protons): 1.08 (d, J=6.48 Hz, 3H), 2.16-2.38 (m, 2H), 3.64 (broad d, J=7.8 Hz, 1H), 5.32 (m, 1H).

1st minority isomers (characteristic protons): 1.12 (d, J=6.78 Hz, 3H), 1.80-1.92 (m, 2H), 3.74 (d, J=3.75 Hz, 1H), 5.45 (m, 1H).

2nd minority isomers (characteristic protons): 0.99 (d, J=6.87 Hz, 3H), 2.38-2.61 (2H), 3.55 (d, J=4.68 Hz, 1H), 5.42 (m, 1H).

NMR-$^{13}$C (CDCl$_3$, 75 MHz): 3 observable isomers (2 majority isomers)

1st Majority isomers: δ(ppm) 135.30 (C$^{IV}$), 130.04 & 130.0 (CH), 129.59 (C$^{IV}$), 76.96 (CHOH), 38.28 (CH), 37.92 & 37.85 (CH$_2$), 37.42 & 37.37 (CH$_2$), 36.84 & 36.79 (CH$_2$), 36.09 (CH), 32.3, 32.26, 25.75 (CH$_3$), 24.45 & 24.42 (CH$_2$), 19.28 (CH$_3$), 19.25 (CH$_3$), 17.91 (CH$_3$).

2nd Isomers (characteristic peaks): δ(ppm) 134.39 (C$^{IV}$), 129.52 & 129.44 (CH), 129.58 (C$^{IV}$), 71.77 (CHOH).

Example 29

Preparation of 4-(4,4-dimethylpentan-2-yl)-2,6-dimethylcyclohex-2-enol 4-(4,4-dimethylpentan-2-yl)-2,6-dimethylcyclohex-2-enol is obtained with a yield of 63%, according to example 22, from 4-(4,4-dimethylpentan-2-yl)-2,6-dimethylcyclohex-2-enone (obtained in example 9).

It consists in a mixture of 6 isomers including 3 main isomers (80%) in a ratio of 30:45:25.

B.p.: 90° C./0.4 torr

Olfactive profile: woody, sandalwood, ambery, slightly flowery and musky.

NMR-$^1$H (CDCl$_3$, 200 MHz): 3 observable isomers majoritarily

δ(ppm) common protons 0.8-1.05 (m, 12H), 1.0-1.65 (m, 5H), 1.65-2.50 (m, 2H).

Majority isomers (characteristic protons): 1.09 (d, J=6.31 Hz, 3H), 1.72-1.76 (m, 3H), 3.59-3.68 (m, 1H), 5.25-5.33 (m, 1H).

Minority isomers (characteristic protons): 0.9-1.0 (m, 3H), 1.76-1.80 (m, 3H), 3.86-3.91 and 3.91-3.97 (2m, 1H), 5.34-5.39 and 5.39-5.44 (2m, 1H).

NMR-$^{13}$C (CDCl$_3$, 50 MHz): 4 observable isomers (2 majority isomers)

Majority isomers (characteristic peaks): 136.69 & 136.27 (C$^{IV}$), 129.22 & 128.62 (CH), 77.17 & 77.11 (CHOH), 47.79 & 47.64 (CH$_2$), 43.47 & 43.30 (CH), 38.50 & 38.47 (CH), 33.47 & 32.77 (CH$_2$), 33.24 & 32.91 (CH), 29.97 (3 CH$_3$), 28.79 & 27.91 (C$^{IV}$).

Minority isomers (characteristic peaks): 128.29 & 127.58 (CH), 72.08 & 71.95 (CHOH), 48.80 & 48.52 (CH$_2$), 40.16 & 39.49 (CH), 33.38 & 33.09 (CH), 32.11 & 31.66 (CH), 31.07 & 30.98 (CH$_2$), 29.97 (3 CH$_3$), 28.79 & 27.91 (C$^{IV}$).

Example 30

Preparation of 4-isopropyl-2,6-dimethylcyclohex-2-enol 4-isopropyl-2,6-dimethylcyclohex-2-enol is obtained with a yield of 73%, according to example 22, from 4-isopropyl-2,6-dimethylcyclohex-2-enone (obtained in example 10).

It consists in a mixture of 4 observable isomers including 2 main (86%) in a ratio of 20:80.

B.p.: 60° C./0.48 torr

Olfactive profile: floral, rosey, citronellol.

NMR-$^1$H (CDCl$_3$, 300 MHz): 3 observable isomers, 2 main isomers (20:80)

δ(ppm) common protons 1.3-1.63 (m, 3H), 1.8-2.13 (m, 2H).

Majority isomers (characteristic protons): 0.81 (d, J=6.84 Hz, 3H), 0.84 (d, J=6.78 Hz, 3H), 1.07 (d, J=6.33 Hz, 3H), 1.70-1.74 (m, 3H), Minority isomers (characteristic protons): 0.86 (d, J=6.66 Hz, 3H), 0.88 (d, J=6.69 Hz, 3H), 0.95 (d, J=6.87 Hz, 3H), 1.75-1.78 (m, 3H)

NMR-$^{13}$C (CDCl$_3$, 75 MHz): 2 observable isomers

Majority isomers: δ(ppm) 136.29 (C$^{IV}$), 128.21 (CH), 76.81 (CHOH), 42.27 (CH), 38.23 (CH), 33.24 (CH$_2$), 32.07 (CH), 19.37 (CH$_3$), 19.34 (CH$_3$), 19.31 (CH$_3$), 18.47 (CH$_3$).

Minority isomers: δ(ppm) 135.12 (C$^{IV}$), 127.63 (CH), 71.60 (CHOH), 39.86 (CH), 31.87 (CH), 31.36 (CH), 28.09 (CH$_2$), 20.87 (CH$_3$), 20.50 (CH$_3$), 20.47 (CH$_3$), 15.42 (CH$_3$).

Example 31

Preparation of 2,6-diethyl-4-isopropylcyclohex-2-enol 2,6-diethyl-4-isopropylcyclohex-2-enol is obtained with a yield of 72%, according to example 22, from 2,6-diethyl-4- isopropylcyclohex-2-enone (obtained with a yield of 27% over the 2 steps, according to example 1, from 4-heptanone and 2-methylene-isovaleraldehyde (prepared from isovaleraldehyde)).

It consists in a mixture of 4 observable isomers including 2 main isomers (83%) in a ratio of 46:54.

B.p.: 72° C./0.45 torr

Olfactive profile: woody, fruity.

NMR-$^1$H (CDCl$_3$, 300 MHz): 3 observable isomers, 2 main isomers (45:55)

δ(ppm) common protons 0.81-0.98 (m, 9H), 0.98-1.07 (m, 3H), 1.12-1.43 (m, 2H), 1.43-1.63 (m, 3H), 1.63-1.75 & 1.91-2.04 (m, 1H), 1.76-1.90 (m, 1H), 2.04-2.26 (m, 1H).

Majority isomers (characteristic protons): 3.78 (broad d, J=8.79 Hz, 1H), 5.35 (s, 1H).

1st Minority isomers (characteristic protons): 3.88 (s, 1H), 5.51 (m, 1H).

$2^{nd}$ Minority isomers (characteristic protons): 3.69 (m, 1H), 5.42 (m, 1H).

NMR-$^{13}$C (CDCl$_3$, 75 MHz): 2 observable isomers

Majority isomers: δ(ppm) 141.11 ($C^{IV}$), 126.73 (CH), 68.87 (CHOH), 42.12 (CH), 40.37 (CH), 32.34 (CH), 29.08 (CH$_2$), 25.69 (CH$_2$), 25.65 (CH$_2$), 20.92 (CH$_3$), 19.98 (CH$_3$), 12.87 (CH$_3$), 11.18 (CH$_3$).

2nd Majority isomers: δ(ppm) 142.02 ($C^{IV}$), 126.67 (CH), 73.63 (CHOH), 44.94 (CH), 38.26 (CH), 32.06 (CH), 27.57 (CH$_2$), 25.15 (CH$_2$), 23.73 (CH$_2$), 20.92 (CH$_3$), 19.93 (CH$_3$), 12.89 (CH$_3$), 11.84 (CH$_3$).

Minority isomers (characteristic peaks): 139.88 ($C^{IV}$), 126.97 (CH), 71.08 (CHOH).

Example 32

Preparation of 4-butyl-2,6-dimethylcyclohex-2-enol 4-butyl-2,6-dimethylcyclohex-2-enol is obtained with a yield of 71%, according to example 22, from 4-butyl-2,6-dimethylcyclohex-2-enone (obtained in example 12).

It consists in a mixture of 3 observable isomers including 2 main isomers (89%) in a ratio of 18:82.

B.p.: 90° C./0.5 torr

Olfactive profile: Citrus (candied citrus peel), grapefruit, sulphurous, rhubarb.

NMR-$^1$H (CDCl$_3$, 300 MHz): 3 observable isomers (50:30:30)

δ(ppm) common protons 0.83-0.92 (m, 3H), 1.1-1.36 (m, 6H), 1.36-1.70 (m, 2H), 1.77-1.99 (m, 1H), 1.99-2.77 (m, 1H).

Majority isomers (characteristic protons): 1.06 (d, J=6.51 Hz, 3H), 1.70-1.73 (m, 3H), 3.60 (broad d, J=8.4 Hz, 1H), 5.31 (m, 1H).

1st Minority isomers (characteristic protons): 0.97 (d, J=6.87 Hz, 3H), 1.75-1.77 (m, 3H), 3.72 (broad d, J=2.8 Hz, 1H), 5.51 (m, 1H).

$2^{nd}$ Minority isomers (characteristic protons): 0.93 (d, J=6.96 Hz, 3H), 1.73-1.75 (m, 3H), 3.52 (broad d, J=3.9 Hz, 1H), 5.45 (broad d, J=4.11 Hz, 1H).

NMR-$^{13}$C (CDCl$_3$, 75 MHz): 3 observable isomers

Majority isomers: δ(ppm) 135.48 ($C^{IV}$), 129.84 (CH), 76.82 (CHOH), 38.19 (CH), 37.39 (CH$_2$), 36.33 (CH$_2$), 36.04 (CH), 33.99 (CH$_3$), 28.77 (CH$_2$), 22.81 (CH$_2$), 19.26 (CH$_3$), 14.02 (CH$_3$).

2nd Majority isomers (characteristic peaks): δ(ppm) 134.46 ($C^{IV}$), 129.33 (CH), 71.66 (CHOH), 34.53 (CH$_2$), 29.93 (CH$_2$), 22.84 (CH$_2$).

$2^{nd}$ Minority isomers (characteristic peaks): 133.60 ($C^{IV}$), 129.44 (CH), 74.72 (CHOH).

Example 33

Preparation of 4-hexyl-2,6-dimethylcyclohex-2-enol 4-hexyl-2,6-dimethylcyclohex-2-enol is obtained with a yield of 55%, according to example 22, from 4-hexyl-2,6-dimethylcyclohex-2-enone (obtained in example 13).

It consists in a mixture of 3 observable isomers including 2 main isomers (88%) in a ratio of 17:83.

B.p.: 90° C./0.46 torr

Olfactive profile: fatty alcohol, soapy.

NMR-$^1$H (CDCl$_3$, 300 MHz): 3 observable isomers (50:30:30)

δ(ppm) common protons 0.8-0.88 (m, 3H), 1.06-1.36 (m, 10H), 1.36-1.86 (m, 2H), 1.88-2.12 (m, 1H), 2.12-2.69 (m, 1H).

Majority isomers (characteristic protons): 1.03 (d, J=6.48 Hz, 3H), 1.68-1.70 (m, 3H), 3.56 (broad d, J=8.56 Hz, 1H), 5.28 (m, 1H).

1st Minority isomers (characteristic protons): 0.95 (d, J=6.84 Hz, 3H), 1.73-1.75 (m, 3H), 3.68 (d, J=3.78 Hz, 1H), 5.42 (d, J=3.60 Hz, 1H).

$2^{nd}$ Minority isomers (characteristic protons): 0.91 (d, J=6.93 Hz, 3H), 1.70-1.73 (m, 3H), 3.49 (d, J=4.75 Hz, 1H), 5.38 (m, 1H).

NMR-$^{13}$C (CDCl$_3$, 75 MHz): 3 observable isomers

Majority isomers: δ(ppm) 135.63 ($C^{IV}$), 129.60 (CH), 76.64 (CHOH), 38.05 (CH), 37.42 (CH$_2$), 36.64 (CH$_2$), 36.05 (CH), 34.0 (CH$_3$), 31.78 (CH$_2$), 30.36 (CH$_3$), 29.45 (CH$_2$), 29.43 (CH$_2$), 22.56 (CH$_2$), 13.97 (CH$_3$).

2nd Majority isomers (characteristic peaks): δ(ppm) 134.46 ($C^{IV}$), 129.16 (CH), 71.49 (CHOH).

$2^{nd}$ Minority isomers (characteristic peaks): 133.69 ($C^{IV}$), 130.49 (CH), 74.61 (CHOH).

Example 34

Preparation of 2,2,6,6-tetramethyl-4-((R)-2,2,3-trimethylcyclopent-3-enyl)cyclohex-3-enol 2,2,6,6-tetramethyl-4-((R)-2,2,3-trimethylcyclopent-3-enyl)cyclohex-3-enol is obtained with a yield of 64%, according to example 22, from (R)-2,2,6,6-tetramethyl-4-(2,2,3-trimethylcyclopent-3-enyl)cyclohex-3-enone (obtained in example 14).

It is a mixture of 2 isomers in a ratio 44:56.

B.p.: 100° C./0.5 torr

Olfactive profile: Woody, weak.

NMR-$^1$H (CDCl$_3$, 200 MHz, common protons): δ(ppm) 1.43 (d, J=5.38 Hz, 1H), 1.55-1.62 (m, 3H), 1.72-2.0 (m, 2H), 2.02-2.20 (m, 1H), 2.32-2.45 (m, 1H), 3.31 (d, J=5.53 Hz, 1H), 5.21-5.28 (m, 1H).

Majority isomers: 0.74 (s, 3H), 0.94 (s, 3H), 1.01 (s, 6H), 1.04 (s, 3H), 1.06 (s, 3H), 2.20-2.26 (m, 1H), 5.17 (s, 1H).

Minority isomers: 0.77 (s, 3H), 0.93 (s, 3H), 1.0 (s, 6H), 1.01 (s, 3H), 1.07 (s, 3H), 2.26-2.32 (m, 1H), 5.18 (s, 1H).

NMR-$^{13}$C (CDCl$_3$, 50 MHz): δ(ppm)

Majority isomers: 12.74, 20.67, 20.71, 22.15, 26.70, 29.38, 31.79, 32.71, 35.38, 37.31, 44.30, 48.12, 57.55, 82.54, 121.54, 132.42, 132.81, 147.47.

Minority isomers: 12.74, 20.92, 21.28, 22.33, 26.92, 29.23, 31.63, 33.57, 35.35, 37.26, 42.88, 48.08, 57.16, 82.56, 121.52, 132.98, 133.23, 148.09.

Example 35

Preparation of 2,2,6,6-tetramethyl-4-((S)-2,2,3-trimethylcyclopent-3-enyl)cyclohex-3-enol 2,2,6,6-tetramethyl-4-((S)-2,2,3-trimethylcyclopent-3-enyl)cyclohex-3-enol is obtained with a yield of 91% (97% purity), according to example 22, from (S)-2,2,6,6-tetramethyl-4-(2,2,3-trimethylcyclopent-3-enyl)cyclohex-3-enone (obtained in example 15).

It is a mixture of 2 isomers in a ratio 43:57.
B.p.: 100-103° C./0.5 torr
Olfactive profile: fruity, raspberry.
Similar analyses to those of example 38.

Example 36

Preparation of 4-(4,4-dimethyl pentan-2-yl)-2,2,6,6 tetramethylcyclohex-3-enol 4-(4,4-dimethylpentan-2-yl)-2,2,6,6-tetramethylcyclohex-3-enol is obtained with a yield of 28%, over 2 steps (alkylation according to example 14, followed by reduction of the ketone according to example 22), from cyclohexenone obtained in example 9.

B.p.: 75° C./0.4 torr
Olfactive profile: earthy, musty
NMR-$^1$H (CDCl$_3$, 200 MHz): δ(ppm) 0.88 (s, 9H), 0.88-0.92 (d, 3H), 0.92-0.98 (m, 3H), 1.0-1.05 (m, 3H), 1.3-1.5 (m, 2H), 1.65-1.95 (m, 2H), 2.05-2.30 (m, 1H), 3.28 (d, J=2.19 Hz, 1H), 5.07 (dd, J=4.97, 2.26 Hz, 1H).
NMR-$^{13}$C (CDCl$_3$, 50 MHz): δ(ppm) 138.75 & 138.41 ($C^{IV}$), 129.93 & 128.98 (CH), 82.79 & 82.59 (CHOH), 48.76 & 47.94 (CH$_2$), 40.03 & 39.22 (CH$_2$), 37.55 & 37.07 (CH), 37.03 & 36.96 ($C^{IV}$), 35.02 ($C^{IV}$), 31.33 & 30.98 (CH), 31.25 ($C^{IV}$), 30.02 & 29.88 (3 CH$_3$), 29.24 & 21.99 (CH$_3$), 22.63 (CH$_3$), 20.82 & 20.26 (CH$_3$).

Example 37

Preparation of 4-isopropyl-2,2,6,6-tetramethylcyclohex-3-enol 4-isopropyl-2,2,6,6-tetramethylcyclohex-3-enol is obtained with a yield of 47%, by treating an ethanol solution of 4-isopropyl-2,2,6,6-tetramethylcyclohex-3-enone (obtained in example 19), at 0° C., with NaBH$_4$ (0.5 eq.). Once the transformation is complete (GPC monitoring), the ethanol is evaporated by half and the mixture diluted in methyl and t-butyl ether. A 34% aq. HCl solution is then added and the aqueous phase, decanted, extracted twice with MTBE. The reunited organic phases are washed with a saturated aqueous solution of sodium bicarbonate, then with brine, dried over magnesium sulphate and the solvents are evaporated. The raw product is purified by distillation.

B.p.: 70° C./0.4 torr
Olfactive profile: woody, earthy, camphorated, sweat
NMR-$^1$H (CDCl$_3$, 300 MHz): δ(ppm) 0.89 (s, 3H), 0.93-0.99 (m, 9H), 1.02 (s, 3H), 1.03 (s, 3H), 1.54 (broad s, 1 OH), 1.80 (dd, J=45.77 Hz, J=16.72 Hz, J=2.37 Hz, 2H), 2.12 (hept, J=6.81 Hz, 1H), 3.29 (s, 1H), 5.05 (dd, J=2.40 Hz, J=0.84 Hz, 1H).
NMR-$^{13}$C (CDCl$_3$, 75 MHz): δ(ppm)
138.24 ($C^{IV}$), 128.29 (CH), 82.61 (CHOH), 40.35 (CH$_2$), 36.91 ($C^{IV}$), 34.98 ($C^{IV}$), 34.71 (CH), 31.45 (CH$_3$), 29.16 (CH$_3$), 22.14 (CH$_3$), 21.30 (CH$_3$), 21.02 (CH$_3$), 20.44 (CH$_3$).

Example 38

Preparation of 2,2,6,6-tetramethyl-4-(2,3,3-trimethylcyclopent-1-enyl)cyclohex-3-enol 2,2,6,6-tetramethyl-4-(2,3,3-trimethylcyclopent-1-enyl)cyclohex-3-enol is obtained by treatment of a 1M solution of 2,2,6,6-tetramethyl-4-((S)-2,2,3-trimethylcyclopent-3-enyl)cyclohex-3-enol (obtained in example 25) with triflic acid at 50° C. Once the reaction is finished (GPC monitoring), the mixture is poured onto a saturated aqueous solution of sodium bicarbonate. The aqueous phase is extracted twice with toluene and the reunited organic phases are washed with brine, dried over magnesium sulphate and the solvents are evaporated. The raw product is distilled to give 2,2,6,6-tetramethyl-4-(2,3,3-trimethylcyclopent-1-enyl)cyclohex-3-enol with a yield of 53%.

B.p.: 100° C./0.5 torr
Olfactive profile: Dusty, raw vegetables, musty
NMR-$^1$H (CDCl$_3$, 200 MHz): δ(ppm) 1.09 (s, 3H), 1.04 (s, 6H), 1.02 (s, 3H), 0.97 (s, 3H), 0.94 (s, 3H), 1.53-1.64 (m, 2H), 1.58-1.60 (m, 3H), 1.80-2.12 (m, 2H), 2.20-2.32 (m, 2H), 3.34 (s, 1H), 5.17 (d, J=2.29 Hz, 1H).
NMR-$^{13}$C (CDCl$_3$, 50 MHz): δ(ppm)
140.08 ($C^{IV}$), 135.11 ($C^{IV}$), 133.62 (CH), 130.64 ($C^{IV}$), 82.25 (CHOH), 47.26 ($C^{IV}$), 42.51 (CH$_2$), 38.61 (CH$_2$), 37.38 ($C^{IV}$), 35.16 ($C^{IV}$), 32.48 (CH$_2$), 31.46 (CH$_3$), 29.15 (CH$_3$), 26.27 (CH$_3$), 26.14 (CH$_3$), 22.19 (CH$_3$), 20.72 (CH$_3$), 10.93 (CH$_3$).

Example 39

Preparation of 2,6-dimethyl-4-(2,2,3-trimethylcyclopentyl)cyclohexanol 2,6-dimethyl-4-(2,2,3-trimethylcyclopentyl)cyclohexanol is obtained according to example 19 from 2,6-dimethyl-4-(2,2,3-trimethylcyclopent-3-enyl)cyclohex-2-enol (obtained in example 22) at 60° C. under 30 bars of H$_2$.

It is a mixture of 8 stereoisomers in a ratio 6:11:12:35:7:5:12:12.
B.p.: 105° C./0.5 torr
Olfactive profile: Aldehyde, fatty, slightly dry woody.
NMR-$^1$H (CDCl$_3$, 200 MHz): δ(ppm) 0.54-0.69 (m, 3H), 0.7-0.85 (m, 3H), 0.85-1.04 (m, 9H), 1.04-1.8 (m, 12H), 1.8-2.12 (m, 2H), 3.19 (dd, J=10.24, 4.89 Hz, 1H) and 3.38-3.54 (m, 1H).
NMR-$^{13}$C (CDCl$_3$, 50 MHz): complex spectrum corresponding to 6 stereoisomers (Characteristic peaks) δ(ppm) 82.87 & 81.80 (majority) & 78.45 & 78.40 & 75.09 & 74.85 (CHOH).

Example 40

Preparation of 1-ethyl-4-isopropyl-2,6-dimethylcyclohex-2-en-1-ol

To a solution in THF of 4-isopropyl-2,6-dimethylcyclohex-2-enone (obtained in example 10) is added, at 0° C., a 1M solution of ethylmagnesium chloride in THF (1.2 eq.). Once the reaction is finished (GPC monitoring), the reaction medium is poured slowly into a methyl and t-butyl ether (MTBE)/10% aq. HCl mixture at 0° C. The aqueous phase is extracted twice with MTBE and the reunited organic phases are washed with a saturated aqueous solution of sodium bicarbonate, then with brine. After drying over magnesium sulphate, filtration on paper and evaporation of the solvents, the raw product is purified by distillation under reduced pressure to give 1-ethyl-4-isopropyl-2,6-dimethyl-cyclohex-2-en-1-ol with a yield of 66%.

It is a mixture of stereoisomers including 4 main isomers (71%) in a ratio 44:14:28:14.

B.p.: 67° C./0.4 torr

Olfactive profile: Woody, camphorated, slightly musty

NMR-$^1$H (CDCl$_3$, 200 MHz): δ(ppm) 0.60-1.15 (m, 12H), 1.15-1.65 (m, 4H), 1.65-1.80 (m, 3H), 1.80-2.25 (m, 2H), 2.25-3.0 (m, 1H), 5.35 & 5.42 & 5.49 (m, 1H).

NMR-$^{13}$C (CDCl$_3$, 50 MHz): complex spectrum corresponding to 6 stereoisomers (Characteristic peaks) δ(ppm) 131.85 (CH, majo), 105.46 ($C^{IV}$, majo).

Example 41

Preparation of 2,6-dimethyl-4-(2,2,3-trimethylcyclopent-3-enyl)cyclohex-2-enyl acetate 2,6-dimethyl-4-(2,2,3-trimethylcyclopent-3-enyl)cyclohex-2-enyl acetate is obtained by treating 2,6-dimethyl-4-(2,2,3-trimethylcyclopent-3-enyl)cyclohex-2-enol (obtained in example 19) with 1.2 molar equivalent of acetic anhydride and a catalytic quantity of N,N-dimethylaminopyridine. After 2 hours at ambient temperature, the excess acetic anhydride and the acetic acid formed during the reaction are eliminated under reduced pressure. The raw product is diluted with methyl and t-butyl ether and the organic phase is washed twice with water, then with a saturated aqueous solution of sodium bicarbonate and lastly with brine. After drying over magnesium sulphate, the solvents are evaporated and the raw product is distilled to give 2,6-dimethyl-4-(2,2,3-trimethylcyclopent-3-enyl)cyclohex-2-enyl acetate with a yield of 73%, in the form of a mixture of 3 main stereoisomers (85%) in a ratio of 25:60:15.

B.p.: 96° C./0.5 torr

Olfactive profile: slightly woody, weak.

NMR analyses corresponding to the expected derivative (to be compared with the corresponding alcohol of example 19).

Example 42

Preparation of 2,6-dimethyl-4-(1-phenylethyl)cyclohex-2-enyl acetate 2,6-dimethyl-4-(1-phenylethyl)cyclohex-2-enyl acetate is obtained with a yield of 75%, according to example 41, from 2,6-dimethyl-4-(1-phenylethyl)cyclohex-2-en-1-ol (obtained with a yield of 72%, according to example 22, from 2,6-dimethyl-4-(1-phenylethyl)cyclohex-2-enone, obtained in example 6).

It is a mixture of 5 observable stereoisomers (91%) in a ratio 12:14:14:25:35.

B.p.: 120° C./0.1 torr

Olfactive profile: flowery, honey-like, crushed lemon pip.

NMR-$^1$H (CDCl$_3$, 300 MHz):

δ(ppm) common protons 0.95-1.22 (m, 1H), 1.37-2.07 (m, 2H), 2.14-2.49 (m, 1H), 2.49-2.73 (m, 1H), 4.87-5.31 (m, 1H), 7.16-7.26 (m, 3H), 7.28-7.37 (m, 2H).

1st Majority isomers (characteristic protons): 0.89 (d, J=6.54 Hz, 3H), 1.33 (d, J=6.90 Hz, 3H), 1.63-1.67 (m, 3H), 5.31-5.37 (m, 1H).

2nd Majority isomers (characteristic protons): 0.98 (d, J=6.45 Hz, 3H), 1.25 (d, J=6.96 Hz, 3H), 1.55-1.59 (m, 3H), 5.65-5.69 (m, 1H).

1st Minority isomers (characteristic protons): 0.83 (d, J=6.71 Hz, 3H), 1.34 (d, J=6.90 Hz, 3H), 1.59-1.62 (m, 3H), 5.82-5.89 (m, 1H).

NMR-$^{13}$C (CDCl$_3$, 75 MHz): 4 observable isomers

Majority isomers: 171.21 (C(O)), 145.46 ($C^{IV}$), 133.87 ($C^{IV}$), 129.52 (CH), 128.1 (CH), 127.44 (CH), 125.89 (CH), 77.84 (CHOAc), 44.44 (CH), 42.67 (CH), 35.41 (CH$_2$), 35.08 (CH), 20.80 (CH$_3$), 19.10 (CH$_3$), 18.62 (CH$_3$), 18.14 (CH$_3$).

1st Minority isomers (characteristic peaks): 145.68 ($C^{IV}$), 133.28 ($C^{IV}$), 129.11 (CH), 77.84 (CHOAc), 33.73 (CH$_2$).

2nd Minority isomers (characteristic peaks): 146.37 ($C^{IV}$), 132.39 ($C^{IV}$), 129.15 (CH), 72.69 (CHOAc), 29.45 (CH$_2$).

Example 43

Preparation of 4-(4,4-dimethylpentan-2-yl)-2,6-dimethylcyclohex-2-enyl acetate 4-(4,4-dimethylpentan-2-yl)-2,6-dimethylcyclohex-2-enyl acetate is obtained with a yield of 60%, according to example 41, from 4-(4,4-dimethylpentan-2-yl)-2,6-dimethylcyclohex-2-en-1-ol (obtained in example 29).

It is a mixture of stereoisomers (5 observed), including 2 main stereoisomers (80%) in a ratio 71:29.

B.p.: 95° C./0.4 torr

Olfactive profile: woody, slightly cocoa, rather similar to the corresponding alcohol, but weaker.

NMR-$^1$H (CDCl$_3$, 200 MHz):

δ(ppm) common protons 0.8-0.95 (m, 15H), 0.95-1.32 (m, 2H), 1.40-1.55 (m, 2H), 1.65-1.90 (m, 1H), 1.90-2.25 (m, 1H).

Majority isomers (characteristic protons): 1.56-1.60 (m, 3H), 2.09 (s, 3H), 5.12-5.22 (m, 1H), 5.42-5.50 (m, 1H).

Minority isomers (characteristic protons): 1.62-1.66 (m, 3H), 2.07 (s, 3H), 5.30-5.40 (m, 2H).

NMR-$^{13}$C (CDCl$_3$, 50 MHz): 4 observable isomers

Majority isomers (characteristic peaks): 171.43 (C(O)), 133.78 & 133.39 ($C^{IV}$), 130.55 & 130.14 (CH), 78.37 & 78.32 (CHOAc), 47.65 & 47.49 (CH$_2$), 43.28 & 43.13 (CH), 32.83 & 32.43 (CH$_2$), 31.03 & 30.97 ($C^{IV}$), 29.94 (3 CH$_3$).

Minority isomers (characteristic peaks): 171.05 (C(O)), 132.05 & 131.77 ($C^{IV}$), 129.79 & 129.37 (CH), 74.09 & 73.83 (CHOAc), 48.51 & 48.19 (CH$_2$), 39.56 & 38.90 (CH), 31.03 & 30.97 ($C^{IV}$), 29.94 (3 CH$_3$), 29.50 & 28.78 (CH$_2$).

Example 44

Preparation of 4-isopropyl-2,2,6,6-tetramethylcyclohex-3-enyl acetate 4-isopropyl-2,2,6,6-tetramethylcyclohex-3-enyl acetate is obtained with a yield of 53% over 2 steps (reduction according to example 37, followed by esterification according to example 41), from 4-isopropyl-2,2,6,6-tetramethyl-cyclohex-3-en-1-one (obtained in example 17).

B.p.: 75° C./0.4 torr

Olfactive profile: Woody, damp, slightly patchouli

NMR-$^1$H (CDCl$_3$, 200 MHz): δ(ppm) 0.89 (s, 3H), 0.92 (s, 3H), 0.95 (s, 6H), 0.96 (s, 3H), 0.97 (s, 3H), 1.7-2.0 (m, 2H), 2.10 (s, 3H), 2.14 (hept, J=6.82 Hz, 1H), 4.78 (s, 1H), 5.04 (m, 1H).

NMR-$^{13}$C (CDCl$_3$, 50 MHz): δ(ppm) 171.16 (C(O)), 138.52 (C1V), 127.64 (CH), 82.57 (CHOAc), 39.64 (CH$_2$), 36.68 (C1V), 34.75 (CH), 34.62 ($C^{IV}$), 30.89 ($CH_3$), 28.33 ($CH_3$), 23.76 ($CH_3$), 22.38 ($CH_3$), 21.25 ($CH_3$), 21.03 ($CH_3$), 20.93 ($CH_3$).

Example 45

Preparation of 4-isopropyl-2,6-dimethylcyclohexyl acetate 4-isopropyl-2,6-dimethylcyclohexyl acetate is obtained with a yield of 60%, according to example 41, from 4-isopropyl-2,6-dimethylcyclohexanol obtained with a yield of 44%, over 2 steps (hydrogenation according to example 19, followed by reduction of the ketone according to example 37, from cyclohexenone obtained in example 10).

It is a mixture of stereoisomers (4 observed), including 2 main stereoisomers (82%) in a ratio 65:35.

B.p.: 48° C./0.4 torr

Olfactive profile: citrus, grapefruit, slightly rhubarb, then woody, citrus fruit peel, dusty.

NMR-$^1$H (CDCl$_3$, 200 MHz): δ(ppm) common protons 0.75-1.07 (m, 14H), 1.08-1.25 (m, 1H), 1.27-1.9 (m, 5H), Majority isomers (characteristic peaks): δ(ppm) 2.05 (s, 3H), 4.98 (s, 1H).

Minority isomers (characteristic peaks): δ(ppm) 2.06 (s, 3H), 4.26 (t, J=10.30 Hz, 1H).

NMR-$^{13}$C (CDCl$_3$, 50 MHz): δ(ppm)

Majority isomers: δ(ppm) 171.14 (C(O)), 76.11 (CHOAc), 43.38 (CH), 36.0 (CH/$CH_3$), 32.66 (CH), 31.91 ($CH_2$), 19.78 ($CH_3$), 18.19 ($CH_3$).

Minority isomers: δ(ppm) 171.14 (C(O)), 82.99 (CHOAc), 42.62 (CH), 37.30 (CH/$CH_3$), 36.93 ($CH_2$), 32.23 (CH), 19.76 ($CH_3$), 18.50 ($CH_3$).

Example 46

Preparation of 4-(4,4-dimethylpentan-2-yl)-1-methoxy-2,6-dimethylcyclohex-2-ene

To a suspension of NaH (1.2 eq.) in THF is added 4-(4,4-dimethylpentan-2-yl)-2,6-dimethylcyclohex-2-en-1-ol. After 4 hours at ambient temperature (end of emission of gas), the mixture is cooled to 0° C. and methyl iodide (1.2 eq.) is added slowly, drop by drop, the reaction medium is then heated to 40° C. over one night. Once the reaction is complete (GPC monitoring), the reaction mixture is poured into a methyl and t-butyl ether (MTBE)/10% aq. HCl mixture. The aqueous phase is extracted twice with MTBE and the reunited organic phases are washed with a 10% aqueous solution of sodium thiosulphate, then with a saturated aqueous solution of sodium bicarbonate and with brine. After drying over magnesium sulphate, filtration on paper and evaporation of the solvents, the raw product is purified by distillation under reduced pressure to give 1-(4,4-dimethylpentan-2-yl)-1-methoxy-2,6-dimethylcyclohex-2-ene with a yield of 57%.

It is a mixture of stereoisomers (8 observed), including 4 main stereoisomers (88%) in a ratio 18:17:33:32.

B.p.: 74° C./0.4 torr

Olfactive profile: woody, chocolate

NMR-$^1$H (CDCl$_3$, 200 MHz, common protons): δ(ppm) 0.8-0.92 (m, 13H), 0.92-1.07 (m, 3H), 1.07-1.4 (m, 2H), 1.4-1.65 (m, 2H).

Majority isomers (characteristic protons): 1.68-1.72 (m, 3H), 3.28 & 3.29 (s, 3H), 3.37-3.42 & 3.42-3.47 (m, 1H), 5.24-5.3 & 5.3-5.34 (m, 1H).

Minority isomers (characteristic protons): 1.71-1.75 (m, 3H), 3.37 & 3.38 (s, 3H), 3.57-3.67 (m, 1H), 5.34-5.38 (m, 1H).

NMR-$^{13}$C (CDCl$_3$, 50 MHz): δ(ppm)

Majority isomers: 135.95 & 135.49 ($C^{IV}$), 130.72 & 130.09 (CH), 85.42 & 85.39 (CHOMe), 55.40 & 55.27 (OCH$_3$), 47.80 & 47.68 (CH$_2$), 43.49 & 43.32 (CH), 33.84 & 33.79 (CH), 33.65 & 32.97 (CH$_2$), 33.26 & 32.93 (CH), 30.99 ($C^{IV}$), 29.97 (3CH$_3$), 19.48 (2(CH$_3$)), 19.33 (2(CH$_3$)), 19.27 & 18.97 (CH$_3$).

Minority isomers: 134.59 & 134.27 ($C^{IV}$), 127.41 & 126.91 (CH), 81.57 & 81.54 (CHOMe), 57.45 & 57.19 (OCH$_3$), 48.19 & 48.01 (CH$_2$), 39.01 & 38.50 (CH), 33.21 & 32.93 (CH), 30.99 & 29.36 (CH$_2$), 30.99 ($C^{IV}$), 29.97 (3CH$_3$), 29.26 & 29.21 (CH), 20.29 & 20.22 (CH$_3$), 19.82 & 19.27 (CH$_3$), 13.06 & 12.80 (CH$_3$).

What is claimed is:

1. A compound having the following general formula (II):

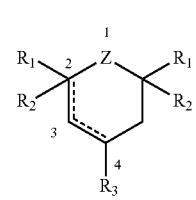

(II)

wherein:
R$_1$ represents a methyl or an ethyl;
R$_2$ represents independently a hydrogen or a C$_1$-C$_5$ alkyl or C$_2$-C$_5$ alkenyl group;
R$_3$ represents an alkyl or alkenyl group, optionally substituted by an aryl, or R$_3$ represents a cyclic alkyl comprising 5 to 6 carbon atoms or cyclic alkenyl group, optionally substituted by one or more C$_1$-C$_6$ alkyl groups, it being understood that R$_3$ includes in total 7 to 10 carbon atoms;
Z represents C(O) or CR$_4$(OR$_5$), with
R$_4$ represents a hydrogen or a C$_1$-C$_8$ alkyl or C$_2$-C$_8$ alkenyl group;
R$_5$ represents a hydrogen or C$_1$-C$_8$ alkyl or alkanoyl or C$_2$-C$_8$ alkenyl or alkenoyl group;
knowing that a double bond is present or absent in the ring and that when it is present, it is
either in position 2-3 and R$_2$ is absent in position 2,
or in position 3-4 and R$_2$ is present in position 2 and is such as defined above;
said compound being in the form of a stereoisomer or of a mixture of stereoisomers, or of a racemic mixture.

2. The compound according to claim 1 wherein R$_3$ is either a cyclopentyl group substituted by one or more alkyl groups, or a cyclopentenyl group substituted by one or more alkyl groups.

3. The compound according to claim 1 wherein R$_3$ is an alkyl or alkenyl group, optionally substituted by an aryl.

4. The compound according to claim 1 wherein Z=C(O).

5. The compound according to claim 1 wherein Z=CR$_4$(OR$_5$) with R$_4$ represents a hydrogen or a C$_1$-C$_8$ alkyl or C$_2$-C$_8$ alkenyl group, and R$_5$ represents a hydrogen.

6. A composition comprising at least one compound of general formula (II) according to claim 1, in the form of a stereoisomer or of a mixture of stereoisomers, or of a racemic mixture.

7. The composition according to claim 6 further comprising at least one additional fragrancing substance.

8. The composition according to claim 6 wherein the compound of formula (II) is present in a concentration of between 0.1 and 99% by weight relative to the total weight of the composition.

9. The composition according to claim 8 wherein the compound of formula (II) is present in a concentration of between 0.1 and 30% by weight relative to the total weight of the composition.

10. A fragrant agent or a flavoring agent comprising the compound of claim 1 and an acceptable fragrant agent carrier or flavoring agent carrier.

11. A masking agent of odors and/or flavors comprising the compound of claim 1 and an acceptable masking agent carrier.

12. A pharmaceutical, cosmetic, or food composition comprising the compound according to claim 1 in combination with perfuming ingredients, flavoring ingredients, solvents, additives, or fixatives.

13. A method for conferring, modifying, or strengthening the organoleptic properties of a substance, of a composition, or of an article, comprising administering the compound as claimed in claim 1 to said substance, composition, or article.

14. A method for masking or neutralizing an odor comprising administering the compound as claimed in claim 1 as a masking agent or a neutralizing agent for an odor.

* * * * *

UNITED STATES PATENT AND TRADEMARK OFFICE
CERTIFICATE OF CORRECTION

PATENT NO. : 9,975,838 B2
APPLICATION NO. : 15/453597
DATED : May 22, 2018
INVENTOR(S) : Chanot et al.

It is certified that error appears in the above-identified patent and that said Letters Patent is hereby corrected as shown below:

On the Title Page

Item (54) Please change:
"METHOD FOR SYNTHEZISING CYCLOHEXENONES FOR USE IN THE PERFUME INDUSTRY AND COMPOUNDS OBTAINED THEREBY"
To:
-- METHOD FOR SYNTHESIZING CYCLOHEXENONES FOR USE IN THE PERFUME INDUSTRY AND COMPOUNDS OBTAINED THEREBY --

Signed and Sealed this
Twenty-third Day of October, 2018

Andrei Iancu
*Director of the United States Patent and Trademark Office*